(12) United States Patent
Berger et al.

(10) Patent No.: US 12,356,994 B2
(45) Date of Patent: Jul. 15, 2025

(54) ANTIPATHOGENIC POLYPEPTIDES

(71) Applicant: UNIVERSITY OF VIRGINIA PATENT FOUNDATION, Charlottesville, VA (US)

(72) Inventors: Bryan W. Berger, Charlottesville, VA (US); Evan L Eckersley, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 795 days.

(21) Appl. No.: 17/287,410

(22) PCT Filed: Oct. 24, 2019

(86) PCT No.: PCT/US2019/057797
§ 371 (c)(1),
(2) Date: Apr. 21, 2021

(87) PCT Pub. No.: WO2020/086807
PCT Pub. Date: Apr. 30, 2020

(65) Prior Publication Data
US 2021/0386072 A1  Dec. 16, 2021

Related U.S. Application Data

(60) Provisional application No. 62/749,876, filed on Oct. 24, 2018.

(51) Int. Cl.
| | |
|---|---|
| *A01N 63/50* | (2020.01) |
| *A01P 3/00* | (2006.01) |
| *A01P 13/00* | (2006.01) |
| *C12N 9/88* | (2006.01) |

(52) U.S. Cl.
CPC ............... *A01N 63/50* (2020.01); *A01P 3/00* (2021.08); *A01P 13/00* (2021.08); *C12N 9/88* (2013.01)

(58) Field of Classification Search
None
See application file for complete search history.

(56) References Cited

U.S. PATENT DOCUMENTS

| 5,582,825 A | 12/1996 | Sakaguchi et al. |
| 2015/0284703 A1 | 10/2015 | Berger |

OTHER PUBLICATIONS

MacDonald et al. "Engineering broad-spectrum digestion of polyuronides from an exolytic polysaccharide lyase" Biotechnology for Biofuels 9:43. (Year: 2016).*
Eckersley E and Berger B "An engineered polysaccharide lyase to combat harmful algal blooms" Biochemical Engineering Journal 132:225-232. (Year: 2018).*
Anonymous "Control of Nuisance Algal Blooms in Ponds Used to Water Lifestock" The Cattle Site, https://www.thecattlesite.com/articles/3984/control-of-nuisance-algal-blooms-in-ponds-used-to-water-livestock. (Year: 2014).*
Supplemental European Search Report dated Oct. 25, 2022 in related European U.S. Appl. No. 19/875,856, filed Oct. 24, 2019.
Papi M. et al., "Detection of Biofilm-Grown Aspergillus fumigatus by Means of Atomic Force Spectroscopy: Ultrastructural Effects of Alginate Lyase", Microscopy and Microanalysis, vol. 18, No. 5, Oct. 1, 2012, pp. 1088-1094; DOI: 10.1017/S1431927612001067.
International Search Report and Written Opinion dated Mar. 5, 2020 in related International Application No. PCT/US2019/057797.
MacDonald, LC et al., "Engineering Broad-Spectrum Digestion of Polyuronides from an Exolytic Polysaccharide Lyase," Biotechnology for Biofuels, vol. 9, No. 43, pp. 1-17; p. 6, col. 1, paragraph 4, Feb. 24, 2016; Genbank Supplemental, p. 4; DOI: 10.1186/s 13068-016-0455-8.
Eckersley, E. et al., "An Engineered Polysaccharide Lyase to Combat Harmful Algal Blooms," Biochemical Engineering Journal. Apr. 15, 2018; vol. 132; pp. 225-232; abstract; DOI: 10.1016/j.bej.2018.01 .005.

* cited by examiner

*Primary Examiner* — Melissa L Fisher
*Assistant Examiner* — Zachary J Miknis
(74) *Attorney, Agent, or Firm* — Dinsmore & Shohl LLP

(57) ABSTRACT

Antipathogenic polypeptides and related compounds and compositions that display antipathogenic activity, antifungal activity (i.e., act as fungicides), antialgal activity (i.e., act as algaecides), and/or enzymatic activity against chitin (i.e., degrade chitin) and/or polyglucuronic acid (i.e., degrade the polyglucuronic acid) are described. These antipathogenic polypeptides, as well the related compounds and compositions disclosed herein, can be used in protecting/treating products, including but not limited to agricultural products and water bodies (including drinking water), from pathogens, including fungi and algae, as well as generating pathogen-resistant products (particularly fungi-resistant and/or algae-resistant products).

17 Claims, 3 Drawing Sheets
Specification includes a Sequence Listing.

SEQUENCE LISTING

```
<160> NUMBER OF SEQ ID NOS: 6

<210> SEQ ID NO 1
<211> LENGTH: 742
<212> TYPE: PRT
<213> ORGANISM: Stenotrophomonas maltophilia

<400> SEQUENCE: 1

Met Arg Leu Gln Pro Leu Phe Val Ser Leu Ala Leu Ala Ala Pro Cys
1               5                   10                  15

Ala Leu Leu Pro Thr Ala Ser Leu Ser Ala Ala Pro Ala Ala Ala Ala
            20                  25                  30

Arg Gln Ala Asp Thr Ala Pro Val Leu Val Thr Ala Ala Gln Trp Gln
        35                  40                  45

Gln Met Ala Ser Glu Gly Arg Arg Tyr Pro Trp Phe Ala Lys Glu Gln
    50                  55                  60

Ala Arg Thr Glu Ala Thr Leu Lys Lys Met Met Lys Ala Gly Ile Asp
65                  70                  75                  80

Val Pro Val Pro Arg Asp Lys Gly Gly Gly Arg Thr His Glu Gln His
                85                  90                  95

Lys Arg Asn Tyr Gln Ala Leu Leu Ala Ala Gly Thr Leu Tyr Arg Leu
            100                 105                 110

Thr Gly Asp Arg Ala Tyr Val Asp Tyr Ala Arg Asp Met Leu Leu Gln
        115                 120                 125

Tyr Ala Gln Leu Tyr Pro Thr Leu Gly Pro His Pro Glu Gly Arg Gly
    130                 135                 140

Gln Ile Pro Gly Arg Val Phe Trp Gln Val Leu Asn Asp Ser Val Trp
145                 150                 155                 160

Leu Val Asn Ala Ile Gln Gly Tyr Asp Ala Ile Arg Asp Ala Leu Ser
                165                 170                 175

Ala Glu Asp Arg Asn Thr Ile Glu Ser Lys Val Phe Arg Pro Met Ala
            180                 185                 190

Glu Phe Leu Val Ser Glu Pro Lys Asn Tyr Asp Gln Ile His Asn His
        195                 200                 205
```

```
Ala Thr Trp Ala Val Ala Ala Thr Gly Met Thr Gly Tyr Val Leu Arg
    210                 215                 220
Asp Gln Glu Leu Val Glu Lys Ser Leu Arg Gly Ser Gln Lys Asp Asp
225                 230                 235                 240
Lys Phe Gly Phe Leu Arg Gln Ile Asp Leu Leu Phe Ser Pro Asp Gly
                245                 250                 255
Tyr Tyr Glu Glu Gly Pro Tyr Tyr Gln Arg Tyr Ala Leu Ala Pro Phe
            260                 265                 270
Leu Leu Phe Ala Asn Ala Ile Glu Arg Asn Glu Pro Gln Arg Lys Ile
        275                 280                 285
Phe Ala Arg Arg Asp Gly Val Leu Leu Lys Ala Val Asp Val Leu Val
    290                 295                 300
Gln Ser Ser Tyr Gly Gly Leu Phe Phe Pro Ile Asn Asp Ala Ile Leu
305                 310                 315                 320
Asp Lys Gly Ile Asp Thr Glu Glu Leu Val Ala Gly Ile Gly Ile Ala
                325                 330                 335
Tyr Ala Arg Thr Gly Asp Asp Arg Leu Leu Ser Val Ala Glu Gln Gln
            340                 345                 350
Lys Arg Leu Leu Leu Ser Pro Glu Gly Leu Gln Val Ala Gln Ala Leu
        355                 360                 365
Ala Ala Asn Lys Ala Lys Pro Phe Asp Tyr His Pro Met Leu Leu Arg
    370                 375                 380
Asp Gly Pro Asp Gly Asp Arg Gly Gly Leu Ala Ile Leu Arg Met Asn
385                 390                 395                 400
Gly Glu Arg Gly Gln Ala Leu Val Gln Lys Asp Thr Met Gln Gly Met
                405                 410                 415
Gly His Gly His Phe Asp Lys Leu Asn Trp Leu Phe Tyr Asp Asn Gly
            420                 425                 430
Asn Pro Val Val Thr Asp Tyr Gly Ala Ala Arg Phe Leu Asn Val Glu
        435                 440                 445
Ala Lys Arg Gly Gly Ile Tyr Leu Ala Glu Asn Arg Ser Trp Ala Lys
    450                 455                 460
Gln Thr Val Ala His Asn Thr Leu Val Val Asp Glu Gln Ser His Phe
465                 470                 475                 480
Asn Gly Asn Trp Lys Arg Gly Glu Ala His Ala Pro Gln Val Arg Phe
                485                 490                 495
Phe Gln Ala Asp Ala Asp Thr Gln Ile Ala Ser Ala Thr Met Arg Asp
            500                 505                 510
Ala Tyr Pro Gly Val Ala Phe Thr Arg Thr Gln Ala Leu Leu Arg His
        515                 520                 525
Pro Asp Leu Gly Leu Pro Val Val Leu Asp Leu Leu Gln Val His Gly
    530                 535                 540
Asp Lys Ala Ala Arg Tyr Asp Leu Pro Leu His Phe Asn Gly His Ile
545                 550                 555                 560
Val Thr Thr Gly Phe Glu Ala Glu His Phe Pro Ser Gln Arg Pro Val
                565                 570                 575
Leu Gly Lys Asp Asn Gly Tyr Gln His Leu Trp Leu Asp Ala Arg Ser
            580                 585                 590
Lys Pro Gly Ser Glu Pro Arg Ser Leu Ala Trp Leu Leu Asp Gly Arg
        595                 600                 605
Phe Tyr Thr Tyr Arg Phe Gly Ser Ser Ala Pro Ala Gln Ala Leu Leu
    610                 615                 620
```

```
Val Glu Ser Gly Ala Asn Asp Pro Glu Phe Asn Leu Arg Arg Glu Pro
625                 630                 635                 640

Ala Leu Leu Gln Arg Val Asp Gly Gln Lys Asp Val Thr Phe Phe Ser
            645                 650                 655

Val Leu Glu Pro His Gly Glu Tyr Asn Gly Thr Ala Glu Tyr Val His
            660                 665                 670

Gly Ala Asp Ser Arg Ile Arg Glu Ile Val Arg Thr Arg Gly Ser Asp
            675                 680                 685

Ala Glu Val Ile Glu Leu Arg Leu Ala Ser Gly Ala Arg Ile Ala Leu
690                 695                 700

Gly Val Ala Asp Asn Ser Ala Thr Thr Ser Glu His Ser Val Thr Val
705                 710                 715                 720

Asp Gly His Val Tyr Arg Trp Asn Gly Ser His Ala Arg Leu Asp Arg
                725                 730                 735

Ser Lys Gly Asp Gly Lys
                740

<210> SEQ ID NO 2
<211> LENGTH: 742
<212> TYPE: PRT
<213> ORGANISM: Artificial Sequence
<220> FEATURE:
<223> OTHER INFORMATION: Synthesized - Modified Stenotrophomonas
      maltophilia (Smlt2602) (W152F)

<400> SEQUENCE: 2

Met Arg Leu Gln Pro Leu Phe Val Ser Leu Ala Leu Ala Ala Pro Cys
1               5                   10                  15

Ala Leu Leu Pro Thr Ala Ser Leu Ser Ala Ala Pro Ala Ala Ala
            20                  25                  30

Arg Gln Ala Asp Thr Ala Pro Val Leu Val Thr Ala Ala Gln Trp Gln
            35                  40                  45

Gln Met Ala Ser Glu Gly Arg Arg Tyr Pro Trp Phe Ala Lys Glu Gln
        50                  55                  60

Ala Arg Thr Glu Ala Thr Leu Lys Lys Met Met Lys Ala Gly Ile Asp
65              70                  75                  80

Val Pro Val Pro Arg Asp Lys Gly Gly Arg Thr His Glu Gln His
                85                  90                  95

Lys Arg Asn Tyr Gln Ala Leu Leu Ala Ala Gly Thr Leu Tyr Arg Leu
                100                 105                 110

Thr Gly Asp Arg Ala Tyr Val Asp Tyr Ala Arg Asp Met Leu Leu Gln
            115                 120                 125

Tyr Ala Gln Leu Tyr Pro Thr Leu Gly Pro His Pro Glu Gly Arg Gly
        130                 135                 140

Gln Ile Pro Gly Arg Val Phe Phe Gln Val Leu Asn Asp Ser Val Trp
145                 150                 155                 160

Leu Val Asn Ala Ile Gln Gly Tyr Asp Ala Ile Arg Asp Ala Leu Ser
                165                 170                 175

Ala Glu Asp Arg Asn Thr Ile Glu Ser Lys Val Phe Arg Pro Met Ala
            180                 185                 190

Glu Phe Leu Val Ser Glu Pro Lys Asn Tyr Asp Gln Ile His Asn His
        195                 200                 205

Ala Thr Trp Ala Val Ala Ala Thr Gly Met Thr Gly Tyr Val Leu Arg
    210                 215                 220

Asp Gln Glu Leu Val Glu Lys Ser Leu Arg Gly Ser Gln Lys Asp Asp
225                 230                 235                 240
```

```
Lys Phe Gly Phe Leu Arg Gln Ile Asp Leu Leu Phe Ser Pro Asp Gly
                245                 250                 255

Tyr Tyr Glu Glu Gly Pro Tyr Tyr Gln Arg Tyr Ala Leu Ala Pro Phe
            260                 265                 270

Leu Leu Phe Ala Asn Ala Ile Glu Arg Asn Glu Pro Gln Arg Lys Ile
            275                 280                 285

Phe Ala Arg Arg Asp Gly Val Leu Leu Lys Ala Val Asp Val Leu Val
    290                 295                 300

Gln Ser Ser Tyr Gly Gly Leu Phe Phe Pro Ile Asn Asp Ala Ile Leu
305                 310                 315                 320

Asp Lys Gly Ile Asp Thr Glu Glu Leu Val Ala Gly Ile Gly Ile Ala
                325                 330                 335

Tyr Ala Arg Thr Gly Asp Asp Arg Leu Leu Ser Val Ala Glu Gln Gln
            340                 345                 350

Lys Arg Leu Leu Leu Ser Pro Glu Gly Leu Gln Val Ala Gln Ala Leu
            355                 360                 365

Ala Ala Asn Lys Ala Lys Pro Phe Asp Tyr His Pro Met Leu Leu Arg
    370                 375                 380

Asp Gly Pro Asp Gly Asp Arg Gly Gly Leu Ala Ile Leu Arg Met Asn
385                 390                 395                 400

Gly Glu Arg Gly Gln Ala Leu Val Gln Lys Asp Thr Met Gln Gly Met
                405                 410                 415

Gly His Gly His Phe Asp Lys Leu Asn Trp Leu Phe Tyr Asp Asn Gly
            420                 425                 430

Asn Pro Val Val Thr Asp Tyr Gly Ala Ala Arg Phe Leu Asn Val Glu
            435                 440                 445

Ala Lys Arg Gly Gly Ile Tyr Leu Ala Glu Asn Arg Ser Trp Ala Lys
    450                 455                 460

Gln Thr Val Ala His Asn Thr Leu Val Val Asp Glu Gln Ser His Phe
465                 470                 475                 480

Asn Gly Asn Trp Lys Arg Gly Glu Ala His Ala Pro Gln Val Arg Phe
                485                 490                 495

Phe Gln Ala Asp Ala Asp Thr Gln Ile Ala Ser Ala Thr Met Arg Asp
            500                 505                 510

Ala Tyr Pro Gly Val Ala Phe Thr Arg Thr Gln Ala Leu Leu Arg His
            515                 520                 525

Pro Asp Leu Gly Leu Pro Val Val Leu Asp Leu Leu Gln Val His Gly
    530                 535                 540

Asp Lys Ala Ala Arg Tyr Asp Leu Pro Leu His Phe Asn Gly His Ile
545                 550                 555                 560

Val Thr Thr Gly Phe Glu Ala Glu His Phe Pro Ser Gln Arg Pro Val
                565                 570                 575

Leu Gly Lys Asp Asn Gly Tyr Gln His Leu Trp Leu Asp Ala Arg Ser
            580                 585                 590

Lys Pro Gly Ser Glu Pro Arg Ser Leu Ala Trp Leu Leu Asp Gly Arg
            595                 600                 605

Phe Tyr Thr Tyr Arg Phe Gly Ser Ser Ala Pro Ala Gln Ala Leu Leu
    610                 615                 620

Val Glu Ser Gly Ala Asn Asp Pro Glu Phe Asn Leu Arg Arg Glu Pro
625                 630                 635                 640

Ala Leu Leu Gln Arg Val Asp Gly Gln Lys Asp Val Thr Phe Phe Ser
                645                 650                 655
```

-continued

Val Leu Glu Pro His Gly Glu Tyr Asn Gly Thr Ala Glu Tyr Val His
                660                 665                 670

Gly Ala Asp Ser Arg Ile Arg Glu Ile Val Arg Thr Arg Gly Ser Asp
            675                 680                 685

Ala Glu Val Ile Glu Leu Arg Leu Ala Ser Gly Ala Arg Ile Ala Leu
        690                 695                 700

Gly Val Ala Asp Asn Ser Ala Thr Thr Ser Glu His Ser Val Thr Val
705                 710                 715                 720

Asp Gly His Val Tyr Arg Trp Asn Gly Ser His Ala Arg Leu Asp Arg
                725                 730                 735

Ser Lys Gly Asp Gly Lys
            740

<210> SEQ ID NO 3
<211> LENGTH: 742
<212> TYPE: PRT
<213> ORGANISM: Artificial Sequence
<220> FEATURE:
<223> OTHER INFORMATION: Synthesized - Modified Stenotrophomonas
      maltophilia (Smlt2602) (Y202F)

<400> SEQUENCE: 3

Met Arg Leu Gln Pro Leu Phe Val Ser Leu Ala Leu Ala Ala Pro Cys
1               5                   10                  15

Ala Leu Leu Pro Thr Ala Ser Leu Ser Ala Ala Pro Ala Ala Ala Ala
            20                  25                  30

Arg Gln Ala Asp Thr Ala Pro Val Leu Val Thr Ala Ala Gln Trp Gln
        35                  40                  45

Gln Met Ala Ser Glu Gly Arg Arg Tyr Pro Trp Phe Ala Lys Glu Gln
    50                  55                  60

Ala Arg Thr Glu Ala Thr Leu Lys Lys Met Met Lys Ala Gly Ile Asp
65                  70                  75                  80

Val Pro Val Pro Arg Asp Lys Gly Gly Gly Arg Thr His Glu Gln His
                85                  90                  95

Lys Arg Asn Tyr Gln Ala Leu Leu Ala Ala Gly Thr Leu Tyr Arg Leu
            100                 105                 110

Thr Gly Asp Arg Ala Tyr Val Asp Tyr Ala Arg Asp Met Leu Leu Gln
        115                 120                 125

Tyr Ala Gln Leu Tyr Pro Thr Leu Gly Pro His Pro Glu Gly Arg Gly
    130                 135                 140

Gln Ile Pro Gly Arg Val Phe Trp Gln Val Leu Asn Asp Ser Val Trp
145                 150                 155                 160

Leu Val Asn Ala Ile Gln Gly Tyr Asp Ala Ile Arg Asp Ala Leu Ser
                165                 170                 175

Ala Glu Asp Arg Asn Thr Ile Glu Ser Lys Val Phe Arg Pro Met Ala
            180                 185                 190

Glu Phe Leu Val Ser Glu Pro Lys Asn Phe Asp Gln Ile His Asn His
        195                 200                 205

Ala Thr Trp Ala Val Ala Ala Thr Gly Met Thr Gly Tyr Val Leu Arg
    210                 215                 220

Asp Gln Glu Leu Val Glu Lys Ser Leu Arg Gly Ser Gln Lys Asp Asp
225                 230                 235                 240

Lys Phe Gly Phe Leu Arg Gln Ile Asp Leu Leu Phe Ser Pro Asp Gly
                245                 250                 255

Tyr Tyr Glu Glu Gly Pro Tyr Tyr Gln Arg Tyr Ala Leu Ala Pro Phe
            260                 265                 270

```
Leu Leu Phe Ala Asn Ala Ile Glu Arg Asn Glu Pro Gln Arg Lys Ile
            275                 280                 285

Phe Ala Arg Arg Asp Gly Val Leu Leu Lys Ala Val Asp Val Leu Val
        290                 295                 300

Gln Ser Ser Tyr Gly Gly Leu Phe Phe Pro Ile Asn Asp Ala Ile Leu
305                 310                 315                 320

Asp Lys Gly Ile Asp Thr Glu Glu Leu Val Ala Gly Ile Gly Ile Ala
                325                 330                 335

Tyr Ala Arg Thr Gly Asp Asp Arg Leu Leu Ser Val Ala Glu Gln Gln
                340                 345                 350

Lys Arg Leu Leu Leu Ser Pro Glu Gly Leu Gln Val Ala Gln Ala Leu
            355                 360                 365

Ala Ala Asn Lys Ala Lys Pro Phe Asp Tyr His Pro Met Leu Leu Arg
        370                 375                 380

Asp Gly Pro Asp Gly Asp Arg Gly Gly Leu Ala Ile Leu Arg Met Asn
385                 390                 395                 400

Gly Glu Arg Gly Gln Ala Leu Val Gln Lys Asp Thr Met Gln Gly Met
                405                 410                 415

Gly His Gly His Phe Asp Lys Leu Asn Trp Leu Phe Tyr Asp Asn Gly
            420                 425                 430

Asn Pro Val Val Thr Asp Tyr Gly Ala Ala Arg Phe Leu Asn Val Glu
        435                 440                 445

Ala Lys Arg Gly Gly Ile Tyr Leu Ala Glu Asn Arg Ser Trp Ala Lys
        450                 455                 460

Gln Thr Val Ala His Asn Thr Leu Val Val Asp Glu Gln Ser His Phe
465                 470                 475                 480

Asn Gly Asn Trp Lys Arg Gly Glu Ala His Ala Pro Gln Val Arg Phe
                485                 490                 495

Phe Gln Ala Asp Ala Asp Thr Gln Ile Ala Ser Ala Thr Met Arg Asp
            500                 505                 510

Ala Tyr Pro Gly Val Ala Phe Thr Arg Thr Gln Ala Leu Leu Arg His
        515                 520                 525

Pro Asp Leu Gly Leu Pro Val Val Leu Asp Leu Leu Gln Val His Gly
        530                 535                 540

Asp Lys Ala Ala Arg Tyr Asp Leu Pro Leu His Phe Asn Gly His Ile
545                 550                 555                 560

Val Thr Thr Gly Phe Glu Ala Glu His Phe Pro Ser Gln Arg Pro Val
                565                 570                 575

Leu Gly Lys Asp Asn Gly Tyr Gln His Leu Trp Leu Asp Ala Arg Ser
            580                 585                 590

Lys Pro Gly Ser Glu Pro Arg Ser Leu Ala Trp Leu Leu Asp Gly Arg
        595                 600                 605

Phe Tyr Thr Tyr Arg Phe Gly Ser Ser Ala Pro Ala Gln Ala Leu Leu
        610                 615                 620

Val Glu Ser Gly Ala Asn Asp Pro Glu Phe Asn Leu Arg Arg Glu Pro
625                 630                 635                 640

Ala Leu Leu Gln Arg Val Asp Gly Gln Lys Asp Val Thr Phe Phe Ser
                645                 650                 655

Val Leu Glu Pro His Gly Glu Tyr Asn Gly Thr Ala Glu Tyr Val His
            660                 665                 670

Gly Ala Asp Ser Arg Ile Arg Glu Ile Val Arg Thr Arg Gly Ser Asp
        675                 680                 685
```

```
Ala Glu Val Ile Glu Leu Arg Leu Ala Ser Gly Ala Arg Ile Ala Leu
        690                 695                 700

Gly Val Ala Asp Asn Ser Ala Thr Thr Ser Glu His Ser Val Thr Val
705                 710                 715                 720

Asp Gly His Val Tyr Arg Trp Asn Gly Ser His Ala Arg Leu Asp Arg
                    725                 730                 735

Ser Lys Gly Asp Gly Lys
            740

<210> SEQ ID NO 4
<211> LENGTH: 742
<212> TYPE: PRT
<213> ORGANISM: Artificial Sequence
<220> FEATURE:
<223> OTHER INFORMATION: Synthesized - Modified Stenotrophomonas
      maltophilia (Smlt2602) (Y202F, H208F)

<400> SEQUENCE: 4

Met Arg Leu Gln Pro Leu Phe Val Ser Leu Ala Leu Ala Ala Pro Cys
1               5                   10                  15

Ala Leu Leu Pro Thr Ala Ser Leu Ser Ala Pro Ala Ala Ala Ala Ala
            20                  25                  30

Arg Gln Ala Asp Thr Ala Pro Val Leu Val Thr Ala Ala Gln Trp Gln
        35                  40                  45

Gln Met Ala Ser Glu Gly Arg Arg Tyr Pro Trp Phe Ala Lys Glu Gln
    50                  55                  60

Ala Arg Thr Glu Ala Thr Leu Lys Lys Met Met Lys Ala Gly Ile Asp
65                  70                  75                  80

Val Pro Val Pro Arg Asp Lys Gly Gly Arg Thr His Glu Gln His
                    85                  90                  95

Lys Arg Asn Tyr Gln Ala Leu Leu Ala Ala Gly Thr Leu Tyr Arg Leu
                100                 105                 110

Thr Gly Asp Arg Ala Tyr Val Asp Tyr Ala Arg Asp Met Leu Leu Gln
            115                 120                 125

Tyr Ala Gln Leu Tyr Pro Thr Leu Gly Pro His Pro Glu Gly Arg Gly
        130                 135                 140

Gln Ile Pro Gly Arg Val Phe Trp Gln Val Leu Asn Asp Ser Val Trp
145                 150                 155                 160

Leu Val Asn Ala Ile Gln Gly Tyr Asp Ala Ile Arg Asp Ala Leu Ser
                165                 170                 175

Ala Glu Asp Arg Asn Thr Ile Glu Ser Lys Val Phe Arg Pro Met Ala
            180                 185                 190

Glu Phe Leu Val Ser Glu Pro Lys Asn Phe Asp Gln Ile His Asn Phe
        195                 200                 205

Ala Thr Trp Ala Val Ala Thr Gly Met Thr Gly Tyr Val Leu Arg
    210                 215                 220

Asp Gln Glu Leu Val Glu Lys Ser Leu Arg Gly Ser Gln Lys Asp Asp
225                 230                 235                 240

Lys Phe Gly Phe Leu Arg Gln Ile Asp Leu Leu Phe Ser Pro Asp Gly
                245                 250                 255

Tyr Tyr Glu Glu Gly Pro Tyr Tyr Gln Arg Tyr Ala Leu Ala Pro Phe
            260                 265                 270

Leu Leu Phe Ala Asn Ala Ile Glu Arg Asn Glu Pro Gln Arg Lys Ile
        275                 280                 285

Phe Ala Arg Arg Asp Gly Val Leu Leu Lys Ala Val Asp Val Leu Val
    290                 295                 300
```

```
Gln Ser Ser Tyr Gly Gly Leu Phe Phe Pro Ile Asn Asp Ala Ile Leu
305                 310                 315                 320

Asp Lys Gly Ile Asp Thr Glu Glu Leu Val Ala Gly Ile Gly Ile Ala
                325                 330                 335

Tyr Ala Arg Thr Gly Asp Asp Arg Leu Leu Ser Val Ala Glu Gln Gln
            340                 345                 350

Lys Arg Leu Leu Leu Ser Pro Glu Gly Leu Gln Val Ala Gln Ala Leu
                355                 360                 365

Ala Ala Asn Lys Ala Lys Pro Phe Asp Tyr His Pro Met Leu Leu Arg
        370                 375                 380

Asp Gly Pro Asp Gly Asp Arg Gly Gly Leu Ala Ile Leu Arg Met Asn
385                 390                 395                 400

Gly Glu Arg Gly Gln Ala Leu Val Gln Lys Asp Thr Met Gln Gly Met
                405                 410                 415

Gly His Gly His Phe Asp Lys Leu Asn Trp Leu Phe Tyr Asp Asn Gly
            420                 425                 430

Asn Pro Val Val Thr Asp Tyr Gly Ala Ala Arg Phe Leu Asn Val Glu
                435                 440                 445

Ala Lys Arg Gly Gly Ile Tyr Leu Ala Glu Asn Arg Ser Trp Ala Lys
        450                 455                 460

Gln Thr Val Ala His Asn Thr Leu Val Val Asp Glu Gln Ser His Phe
465                 470                 475                 480

Asn Gly Asn Trp Lys Arg Gly Glu Ala His Ala Pro Gln Val Arg Phe
                485                 490                 495

Phe Gln Ala Asp Ala Asp Thr Gln Ile Ala Ser Ala Thr Met Arg Asp
            500                 505                 510

Ala Tyr Pro Gly Val Ala Phe Thr Arg Thr Gln Ala Leu Leu Arg His
        515                 520                 525

Pro Asp Leu Gly Leu Pro Val Val Leu Asp Leu Leu Gln Val His Gly
    530                 535                 540

Asp Lys Ala Ala Arg Tyr Asp Leu Pro Leu His Phe Asn Gly His Ile
545                 550                 555                 560

Val Thr Thr Gly Phe Glu Ala Glu His Phe Pro Ser Gln Arg Pro Val
                565                 570                 575

Leu Gly Lys Asp Asn Gly Tyr Gln His Leu Trp Leu Asp Ala Arg Ser
            580                 585                 590

Lys Pro Gly Ser Glu Pro Arg Ser Leu Ala Trp Leu Leu Asp Gly Arg
        595                 600                 605

Phe Tyr Thr Tyr Arg Phe Gly Ser Ser Ala Pro Ala Gln Ala Leu Leu
    610                 615                 620

Val Glu Ser Gly Ala Asn Asp Pro Glu Phe Asn Leu Arg Arg Glu Pro
625                 630                 635                 640

Ala Leu Leu Gln Arg Val Asp Gly Gln Lys Asp Val Thr Phe Phe Ser
                645                 650                 655

Val Leu Glu Pro His Gly Glu Tyr Asn Gly Thr Ala Glu Tyr Val His
            660                 665                 670

Gly Ala Asp Ser Arg Ile Arg Glu Ile Val Arg Thr Arg Gly Ser Asp
        675                 680                 685

Ala Glu Val Ile Glu Leu Arg Leu Ala Ser Gly Ala Arg Ile Ala Leu
    690                 695                 700

Gly Val Ala Asp Asn Ser Ala Thr Thr Ser Glu His Ser Val Thr Val
705                 710                 715                 720
```

```
Asp Gly His Val Tyr Arg Trp Asn Gly Ser His Ala Arg Leu Asp Arg
                725                 730                 735

Ser Lys Gly Asp Gly Lys
            740

<210> SEQ ID NO 5
<211> LENGTH: 742
<212> TYPE: PRT
<213> ORGANISM: Artificial Sequence
<220> FEATURE:
<223> OTHER INFORMATION: Synthesized - Modified Stenotrophomonas
      maltophilia (Smlt2602) (Q153A)

<400> SEQUENCE: 5

Met Arg Leu Gln Pro Leu Phe Val Ser Leu Ala Leu Ala Ala Pro Cys
1               5                   10                  15

Ala Leu Leu Pro Thr Ala Ser Leu Ser Ala Ala Pro Ala Ala Ala Ala
            20                  25                  30

Arg Gln Ala Asp Thr Ala Pro Val Leu Val Thr Ala Ala Gln Trp Gln
        35                  40                  45

Gln Met Ala Ser Glu Gly Arg Arg Tyr Pro Trp Phe Ala Lys Glu Gln
    50                  55                  60

Ala Arg Thr Glu Ala Thr Leu Lys Lys Met Met Lys Ala Gly Ile Asp
65                  70                  75                  80

Val Pro Val Pro Arg Asp Lys Gly Gly Arg Thr His Glu Gln His
                85                  90                  95

Lys Arg Asn Tyr Gln Ala Leu Leu Ala Ala Gly Thr Leu Tyr Arg Leu
                100                 105                 110

Thr Gly Asp Arg Ala Tyr Val Asp Tyr Ala Arg Asp Met Leu Leu Gln
            115                 120                 125

Tyr Ala Gln Leu Tyr Pro Thr Leu Gly Pro His Pro Glu Gly Arg Gly
        130                 135                 140

Gln Ile Pro Gly Arg Val Phe Trp Ala Val Leu Asn Asp Ser Val Trp
145                 150                 155                 160

Leu Val Asn Ala Ile Gln Gly Tyr Asp Ala Ile Arg Asp Ala Leu Ser
                165                 170                 175

Ala Glu Asp Arg Asn Thr Ile Glu Ser Lys Val Phe Arg Pro Met Ala
            180                 185                 190

Glu Phe Leu Val Ser Glu Pro Lys Asn Tyr Asp Gln Ile His Asn His
        195                 200                 205

Ala Thr Trp Ala Val Ala Ala Thr Gly Met Thr Gly Tyr Val Leu Arg
    210                 215                 220

Asp Gln Glu Leu Val Glu Lys Ser Leu Arg Gly Ser Gln Lys Asp Asp
225                 230                 235                 240

Lys Phe Gly Phe Leu Arg Gln Ile Asp Leu Leu Phe Ser Pro Asp Gly
                245                 250                 255

Tyr Tyr Glu Glu Gly Pro Tyr Tyr Gln Arg Tyr Ala Leu Ala Pro Phe
            260                 265                 270

Leu Leu Phe Ala Asn Ala Ile Glu Arg Asn Glu Pro Gln Arg Lys Ile
        275                 280                 285

Phe Ala Arg Arg Asp Gly Val Leu Leu Lys Ala Val Asp Val Leu Val
    290                 295                 300

Gln Ser Ser Tyr Gly Gly Leu Phe Phe Pro Ile Asn Asp Ala Ile Leu
305                 310                 315                 320

Asp Lys Gly Ile Asp Thr Glu Glu Leu Val Ala Gly Ile Gly Ile Ala
                325                 330                 335
```

```
Tyr Ala Arg Thr Gly Asp Asp Arg Leu Leu Ser Val Ala Glu Gln Gln
            340                 345                 350

Lys Arg Leu Leu Leu Ser Pro Glu Gly Leu Gln Val Ala Gln Ala Leu
            355                 360                 365

Ala Ala Asn Lys Ala Lys Pro Phe Asp Tyr His Pro Met Leu Leu Arg
            370                 375                 380

Asp Gly Pro Asp Gly Arg Gly Leu Ala Ile Leu Arg Met Asn
385                 390                 395                 400

Gly Glu Arg Gly Gln Ala Leu Val Gln Lys Asp Thr Met Gln Gly Met
                405                 410                 415

Gly His Gly His Phe Asp Lys Leu Asn Trp Leu Phe Tyr Asp Asn Gly
            420                 425                 430

Asn Pro Val Val Thr Asp Tyr Gly Ala Ala Arg Phe Leu Asn Val Glu
            435                 440                 445

Ala Lys Arg Gly Gly Ile Tyr Leu Ala Glu Asn Arg Ser Trp Ala Lys
            450                 455                 460

Gln Thr Val Ala His Asn Thr Leu Val Val Asp Glu Gln Ser His Phe
465                 470                 475                 480

Asn Gly Asn Trp Lys Arg Gly Glu Ala His Ala Pro Gln Val Arg Phe
            485                 490                 495

Phe Gln Ala Asp Ala Asp Thr Gln Ile Ala Ser Ala Thr Met Arg Asp
            500                 505                 510

Ala Tyr Pro Gly Val Ala Phe Thr Arg Thr Gln Ala Leu Leu Arg His
            515                 520                 525

Pro Asp Leu Gly Leu Pro Val Val Leu Asp Leu Gln Val His Gly
            530                 535                 540

Asp Lys Ala Ala Arg Tyr Asp Leu Pro Leu His Phe Asn Gly His Ile
545                 550                 555                 560

Val Thr Thr Gly Phe Glu Ala Glu His Phe Pro Ser Gln Arg Pro Val
                565                 570                 575

Leu Gly Lys Asp Asn Gly Tyr Gln His Leu Trp Leu Asp Ala Arg Ser
            580                 585                 590

Lys Pro Gly Ser Glu Pro Arg Ser Leu Ala Trp Leu Leu Asp Gly Arg
            595                 600                 605

Phe Tyr Thr Tyr Arg Phe Gly Ser Ser Ala Pro Ala Gln Ala Leu Leu
            610                 615                 620

Val Glu Ser Gly Ala Asn Asp Pro Glu Phe Asn Leu Arg Arg Glu Pro
625                 630                 635                 640

Ala Leu Leu Gln Arg Val Asp Gly Gln Lys Asp Val Thr Phe Phe Ser
                645                 650                 655

Val Leu Glu Pro His Gly Glu Tyr Asn Gly Thr Ala Glu Tyr Val His
            660                 665                 670

Gly Ala Asp Ser Arg Ile Arg Glu Ile Val Arg Thr Arg Gly Ser Asp
            675                 680                 685

Ala Glu Val Ile Glu Leu Arg Leu Ala Ser Gly Ala Arg Ile Ala Leu
            690                 695                 700

Gly Val Ala Asp Asn Ser Ala Thr Thr Ser Glu His Ser Val Thr Val
705                 710                 715                 720

Asp Gly His Val Tyr Arg Trp Asn Gly Ser His Ala Arg Leu Asp Arg
                725                 730                 735

Ser Lys Gly Asp Gly Lys
            740
```

<210> SEQ ID NO 6
<211> LENGTH: 742
<212> TYPE: PRT
<213> ORGANISM: Artificial Sequence
<220> FEATURE:
<223> OTHER INFORMATION: Synthesized - Modified Stenotrophomonas maltophilia (Smlt2602) (Y455F)

<400> SEQUENCE: 6

```
Met Arg Leu Gln Pro Leu Phe Val Ser Leu Ala Leu Ala Ala Pro Cys
1               5                   10                  15

Ala Leu Leu Pro Thr Ala Ser Leu Ser Ala Pro Ala Ala Ala Ala Ala
                20                  25                  30

Arg Gln Ala Asp Thr Ala Pro Val Leu Val Thr Ala Ala Gln Trp Gln
            35                  40                  45

Gln Met Ala Ser Glu Gly Arg Arg Tyr Pro Trp Phe Ala Lys Glu Gln
    50                  55                  60

Ala Arg Thr Glu Ala Thr Leu Lys Lys Met Met Lys Ala Gly Ile Asp
65                  70                  75                  80

Val Pro Val Pro Arg Asp Lys Gly Gly Gly Arg Thr His Glu Gln His
                85                  90                  95

Lys Arg Asn Tyr Gln Ala Leu Leu Ala Ala Gly Thr Leu Tyr Arg Leu
            100                 105                 110

Thr Gly Asp Arg Ala Tyr Val Asp Tyr Ala Arg Asp Met Leu Leu Gln
        115                 120                 125

Tyr Ala Gln Leu Tyr Pro Thr Leu Gly Pro His Pro Glu Gly Arg Gly
    130                 135                 140

Gln Ile Pro Gly Arg Val Phe Trp Gln Val Leu Asn Asp Ser Val Trp
145                 150                 155                 160

Leu Val Asn Ala Ile Gln Gly Tyr Asp Ala Ile Arg Asp Ala Leu Ser
                165                 170                 175

Ala Glu Asp Arg Asn Thr Ile Glu Ser Lys Val Phe Arg Pro Met Ala
            180                 185                 190

Glu Phe Leu Val Ser Glu Pro Lys Asn Tyr Asp Gln Ile His Asn His
        195                 200                 205

Ala Thr Trp Ala Val Ala Ala Thr Gly Met Thr Gly Tyr Val Leu Arg
    210                 215                 220

Asp Gln Glu Leu Val Glu Lys Ser Leu Arg Gly Ser Gln Lys Asp Asp
225                 230                 235                 240

Lys Phe Gly Phe Leu Arg Gln Ile Asp Leu Leu Phe Ser Pro Asp Gly
                245                 250                 255

Tyr Tyr Glu Glu Gly Pro Tyr Tyr Gln Arg Tyr Ala Leu Ala Pro Phe
            260                 265                 270

Leu Leu Phe Ala Asn Ala Ile Glu Arg Asn Glu Pro Gln Arg Lys Ile
        275                 280                 285

Phe Ala Arg Arg Asp Gly Val Leu Leu Lys Ala Val Asp Val Leu Val
    290                 295                 300

Gln Ser Ser Tyr Gly Gly Leu Phe Phe Pro Ile Asn Asp Ala Ile Leu
305                 310                 315                 320

Asp Lys Gly Ile Asp Thr Glu Glu Leu Val Ala Gly Ile Gly Ile Ala
                325                 330                 335

Tyr Ala Arg Thr Gly Asp Asp Arg Leu Leu Ser Val Ala Glu Gln Gln
            340                 345                 350

Lys Arg Leu Leu Leu Ser Pro Glu Gly Leu Gln Val Ala Gln Ala Leu
        355                 360                 365
```

```
Ala Ala Asn Lys Ala Lys Pro Phe Asp Tyr His Pro Met Leu Leu Arg
        370             375                 380

Asp Gly Pro Asp Gly Asp Arg Gly Gly Leu Ala Ile Leu Arg Met Asn
385             390                 395                     400

Gly Glu Arg Gly Gln Ala Leu Val Gln Lys Asp Thr Met Gln Gly Met
                405                 410                 415

Gly His Gly His Phe Asp Lys Leu Asn Trp Leu Phe Tyr Asp Asn Gly
            420                 425                 430

Asn Pro Val Val Thr Asp Tyr Gly Ala Ala Arg Phe Leu Asn Val Glu
            435                 440                 445

Ala Lys Arg Gly Gly Ile Phe Leu Ala Glu Asn Arg Ser Trp Ala Lys
        450                 455                 460

Gln Thr Val Ala His Asn Thr Leu Val Val Asp Glu Gln Ser His Phe
465                 470                 475                 480

Asn Gly Asn Trp Lys Arg Gly Glu Ala His Ala Pro Gln Val Arg Phe
                485                 490                 495

Phe Gln Ala Asp Ala Asp Thr Gln Ile Ala Ser Ala Thr Met Arg Asp
                500                 505                 510

Ala Tyr Pro Gly Val Ala Phe Thr Arg Thr Gln Ala Leu Leu Arg His
            515                 520                 525

Pro Asp Leu Gly Leu Pro Val Val Leu Asp Leu Leu Gln Val His Gly
    530                 535                 540

Asp Lys Ala Ala Arg Tyr Asp Leu Pro Leu His Phe Asn Gly His Ile
545                 550                 555                 560

Val Thr Thr Gly Phe Glu Ala Glu His Phe Pro Ser Gln Arg Pro Val
                565                 570                 575

Leu Gly Lys Asp Asn Gly Tyr Gln His Leu Trp Leu Asp Ala Arg Ser
            580                 585                 590

Lys Pro Gly Ser Glu Pro Arg Ser Leu Ala Trp Leu Leu Asp Gly Arg
        595                 600                 605

Phe Tyr Thr Tyr Arg Phe Gly Ser Ser Ala Pro Ala Gln Ala Leu Leu
    610                 615                 620

Val Glu Ser Gly Ala Asn Asp Pro Glu Phe Asn Leu Arg Arg Glu Pro
625                 630                 635                 640

Ala Leu Leu Gln Arg Val Asp Gly Gln Lys Asp Val Thr Phe Phe Ser
                645                 650                 655

Val Leu Glu Pro His Gly Glu Tyr Asn Gly Thr Ala Glu Tyr Val His
                660                 665                 670

Gly Ala Asp Ser Arg Ile Arg Glu Ile Val Arg Thr Arg Gly Ser Asp
            675                 680                 685

Ala Glu Val Ile Glu Leu Arg Leu Ala Ser Gly Ala Arg Ile Ala Leu
        690                 695                 700

Gly Val Ala Asp Asn Ser Ala Thr Thr Ser Glu His Ser Val Thr Val
705                 710                 715                 720

Asp Gly His Val Tyr Arg Trp Asn Gly Ser His Ala Arg Leu Asp Arg
                725                 730                 735

Ser Lys Gly Asp Gly Lys
            740
```

ANTIPATHOGENIC POLYPEPTIDES

CROSS-REFERENCE TO RELATED APPLICATION

This application is a National Phase application of International Application No. PCT/US2019/057797, filed on Oct. 24, 2019 and depends from and claims the benefit of U.S. Provisional Application No. 62/749,876 filed Oct. 24, 2018, the entire contents of which is incorporated herein by reference.

GOVERNMENT RIGHTS

This invention was made with government support under IIP1801612 awarded by the National Science Foundation. The government has certain rights in the invention.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created Oct. 23, 2019, is named "SEQ LISTING 122305_3_UVA_REF_BERGER_ENZ_0249_02" and is 39 KB bytes in size.

FIELD

The present disclosure generally relates to antipathogenic polypeptides and related compounds and compositions. More particularly, the present disclosure relates to antipathogenic polypeptides and related compounds and compositions that display antipathogenic activity, antifungal activity (i.e., act as fungicides), antialgal activity (i.e., act as algaecides), and/or enzymatic activity against chitin (i.e., degrade chitin) and/or polyglucuronic acid (i.e., degrade the polyglucuronic acid). These antipathogenic polypeptides, as well the related compounds and compositions disclosed herein, can be used in protecting/treating products, including but not limited to agricultural products and water bodies (including drinking water), from pathogens, including fungi and algae, as well as generating pathogen-resistant products (particularly fungi and algae-resistant products).

BACKGROUND

Global agriculture faces immense pressure to meet growing demands for higher yields while suffering increasing losses due to microbial pathogens pre- and post-harvest. Microbial pathogens, including various fungi, have also gained widespread fungicide resistance, requiring several applications of multiple fungicides throughout the season to minimize spread of infection, at a large, continually increasing cost to growers. Moreover, growers and consumers are increasingly aware of the hazards chemical fungicides present to growers, consumers, and the environment, as well as decline in product taste and quality caused by heavy fungicide use, and are demanding organic, green and safe alternatives. Thus, there exists a major market gap for a green, effective solution to alleviate increasing losses to growers and producers.

SUMMARY

Accordingly, the present disclosure is directed to a novel, enzymatic biofungicide and algaecides and related compositions that directly attacks the fungal or algal cell wall to prevent and reduce spread of infection, including the infection of agricultural products pre- and post-harvest. The instantly-disclosed compounds and compositions are a unique solution that address the major market gap for green, safe fungicides and algaecides by (1) significantly inhibiting fungal and algal growth while preventing resistance, (2) exhibiting full activity over one month when applied, reducing the number of applications required in the field, and (3) providing a green, organic product eligible for OMRI/ USDA certification that reduces toxicity, ensures environmental safety, and does not alter product quality or taste. As such, in aspects, the present disclosure provides antipathogenic polypeptides and related compounds and compositions. In aspects, the antipathogenic polypeptides and related compounds and compositions display antipathogenic activity, antifungal activity (i.e., act as fungicides), antialgal activity (i.e., act as algaecides), and/or enzymatic activity against chitin (i.e., degrade chitin) and/or polyglucuronic acid (i.e., degrade the polyglucuronic acid). In aspects, these polypeptides and related compositions display antialgal activity against a wide variety of harmful algae and harmful algal blooms. As such, these antipathogenic polypeptides, as well the related compounds and compositions disclosed herein, can be used in protecting/treating products, including but not limited to agricultural products and water bodies (including drinking water), from pathogens, including fungi and algae, as well as generating pathogen-resistant products (particularly fungi and algae-resistant products).

In aspects, the present disclosure is directed to antipathogenic polypeptides having a an amino acid set forth in SEQ ID NO: 1, SEQ ID NO: 2, SEQ ID NO: 3, SEQ ID NO: 4, SEQ ID NO: 5, or SEQ ID NO: 6, and variants and fragments thereof. In some aspects, the present disclosure is directed to a polypeptide having antipathogenic activity, said polypeptide comprising an amino acid sequence having at least 75%, 80%, 85%, 90%, or 95% homology to SEQ ID NO: 1, SEQ ID NO: 2, SEQ ID NO: 3, SEQ ID NO: 4, SEQ ID NO: 5, or SEQ ID NO: 6, and variants and fragments thereof. In aspects of the above-referenced polypeptides polypeptide having antifungal and/or antialgal activity. In aspects of the above-described polypeptides, the polypeptides may be isolated, synthetic, or recombinant.

In further aspects, the present disclosure is directed to an antipathogenic polypeptide having antipathogenic activity (e.g., antifungal activity), said polypeptide comprising an amino acid sequence having at least 75%, 80%, 85%, 90%, or 95% homology to SEQ ID NO: 2 and further comprising a phenylalanine at amino acid position 152. In aspects, the present disclosure is directed to a polypeptide having antipathogenic activity (e.g., antifungal activity and/or antialgal activity), said polypeptide comprising an amino acid sequence having at least 75%, 80%, 85%, 90%, or 95% homology to SEQ ID NO: 3 and further comprising a phenylalanine at amino acid position 202. In aspects, the present disclosure is directed to a polypeptide having antipathogenic activity (e.g., antifungal activity and/or antialgal activity), said polypeptide comprising an amino acid sequence having at least 75%, 80%, 85%, 90%, or 95% homology to SEQ ID NO: 4 and further comprising a phenylalanine at amino acid position 202 and a phenylalanine at amino acid position 208. In aspects, the present disclosure is directed to a polypeptide having antipathogenic activity (e.g., antifungal activity), said polypeptide comprising an amino acid sequence having at least 75%, 80%, 85%, 90%, or 95% homology to SEQ ID NO: 5 and further comprising an alanine at amino acid position 153. In aspects, the present disclosure is directed to a polypeptide having antipathogenic activity (e.g., antifungal activity), said polypeptide comprising an amino acid sequence having at least 75%, 80%, 85%, 90%, or 95% homology to SEQ ID NO: 6 and further comprising a phenylalanine at amino acid position 455. In aspects of the above-referenced polypeptides polypeptide having antifungal and/or antialgal activity. In aspects, these polypeptides display enzymatic activity against chitin and/or polyglucuronic acid. In aspects of the above-described polypeptides, the polypeptides may be isolated, synthetic, or recombinant.

In some aspects, a genetically modified polysaccharide lyase polypeptide having antipathogenic activity (e.g., antifungal activity) is provided, said polypeptide comprising an amino acid sequence having at least 75%, 80%, 85%, 90%, or 95% homology to SEQ ID NO: 1 and comprising the mutation W152F. In aspects, a genetically modified polysaccharide lyase polypeptide having antipathogenic activity (e.g., antifungal activity and/or antialgal activity) is provided, said polypeptide comprising an amino acid sequence having at least 75%, 80%, 85%, 90%, or 95% homology to SEQ ID NO: 1 and comprising the mutation Y202F. In additional aspects, a genetically modified polysaccharide lyase polypeptide having antipathogenic activity (e.g., antifungal activity and/or antialgal activity) is provided, said polypeptide comprising an amino acid sequence having at least 75%, 80%, 85%, 90%, or 95% homology to SEQ ID NO: 1 and comprising the mutations Y202F and H208F. In further aspects, a genetically modified polysaccharide lyase polypeptide having antipathogenic activity (e.g., antifungal activity) is provided, said polypeptide comprising an amino acid sequence having at least 75%, 80%, 85%, 90%, or 95% homology to SEQ ID NO: 1 and comprising the mutation Q153A. In aspects, a genetically modified polysaccharide lyase polypeptide having antipathogenic activity (e.g., antifungal activity) is provided, said polypeptide comprising an amino acid sequence having at least 75%, 80%, 85%, 90%, or 95% homology to SEQ ID NO: 1 and comprising the mutation Y455F. In aspects of the above-referenced polypeptides polypeptide having antifungal and/or antialgal activity. In aspects, these polypeptides display enzymatic activity against chitin and/or polyglucuronic acid. In aspects of the above-described polypeptides, the polypeptides may be isolated, synthetic, or recombinant.

In aspects, the present disclosure is directed to a polynucleotide (e.g., DNA or RNA) encoding one or more polypeptides of the present disclosure. In aspects of the instantly-disclosed polynucleotides, the polynucleotides may be isolated, synthetic, or recombinant. In aspects, an expression cassette, plasmid, expression vector, and recombinant virus comprising such a polynucleotide is provided. In aspects, a microorganism or cell comprising an expression cassette, plasmid, vector, or recombinant virus of the present disclosure is provided.

In aspects, the present disclosure is directed to an antipathogenic composition comprising: one or more polypeptides, one or more microorganisms that express one or more polypeptides, and/or nucleic acids of the present disclosure; and a carrier and/or excipient. In aspects, the antipathogenic composition my further comprise one or more additional active agents, such as pesticides, fertilizers, insecticides, attractants, sterilizing agents, acaridices, nematocides, herbicides, and/or growth regulators. In aspects, a polypeptide of the present disclosure is present in the antipathogenic composition at a concentration range of from about 0.1 microgram per milliliter to about 100 milligrams per milliliter. In aspects, the pH of the antipathogenic composition of the present disclosure is in the range of from about 4.0 to about 9.0.

In additional aspects, the present disclosure is directed to methods for protecting or treating a product against a pathogen, such as fungi and/or algae. In aspects, the present disclosure is directed to a method of protecting or treating a product against a fungi and/or an algae, said method comprising applying or contacting one or more polypeptides, nucleic acids, expression cassettes, plasmids, expression vectors, recombinant viruses and/or antipathogenic compositions of the present disclosure to the product. In additional aspects, the present disclosure is directed to methods for inducing pathogen resistance in a product, the method comprising applying or contacting one or more compounds or compositions of the present disclosure to the product. In aspects, the product is an agricultural product or a body of water (e.g., drinking water, such as tap water).

These and additional embodiments and features of the presently-disclosed subject matter will be clarified by reference to the figures and detailed description set forth herein.

It is understood that both the preceding summary and the following detailed description are exemplary and are intended to provide further explanation of the disclosure as claimed. Neither the summary nor the description that follows is intended to define or limit the scope of the disclosure to the particular features mentioned in the summary or description.

DETAILED DESCRIPTION

Figure 1:
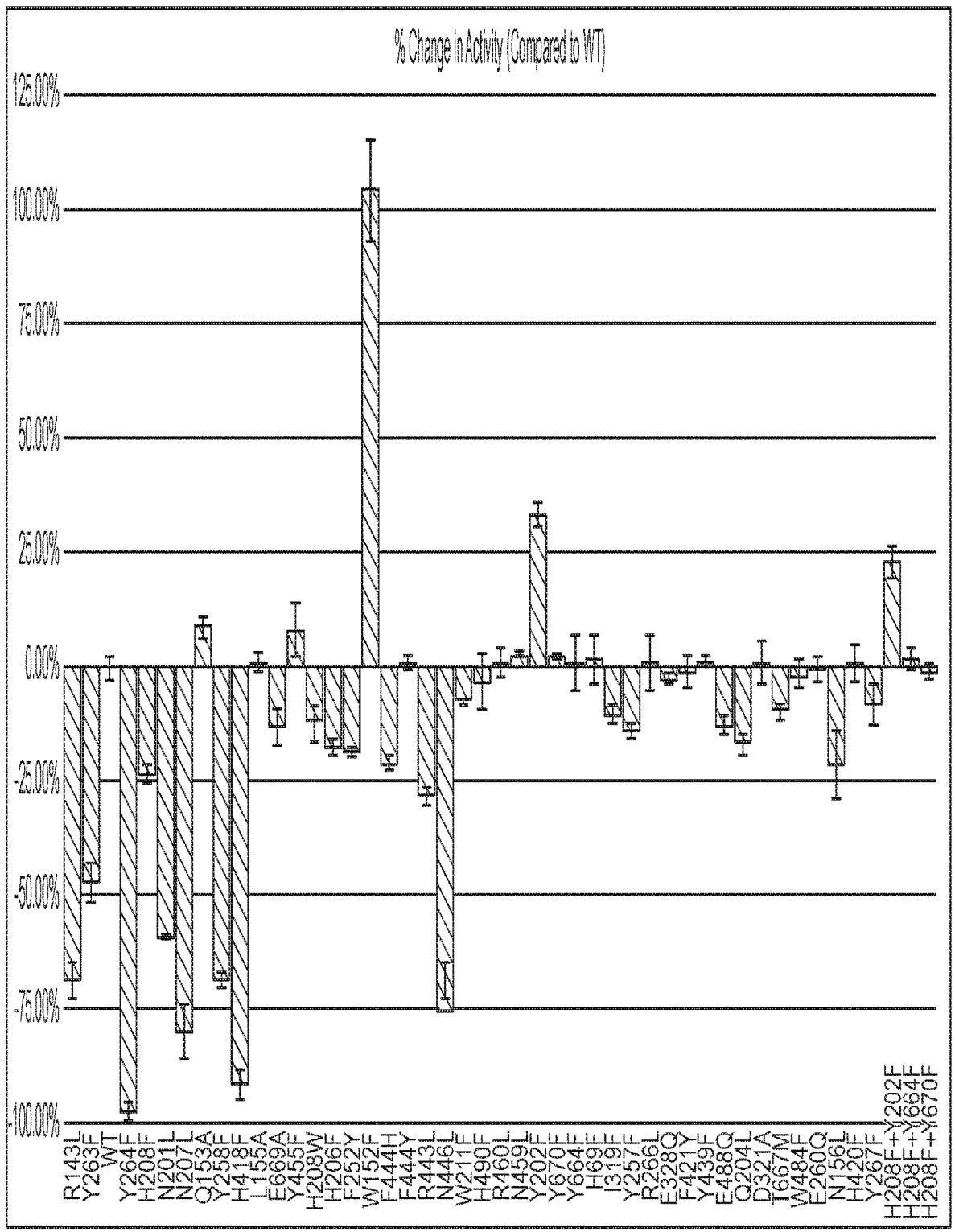
FIG. 1 shows a Schales' assay for antifungal activity screening for the wild type and various genetically modified polysaccharide lyase polypeptides from *Stenotrophomonas maltophilia* (Smlt2602; UniProt ID B2FSW8).

The following description of particular aspect(s) is merely exemplary in nature and is in no way intended to limit the scope of the invention, its application, or uses, which may, of course, vary. The invention is described with relation to the non-limiting definitions and terminology included herein. These definitions and terminology are not designed to function as a limitation on the scope or practice of the invention but are presented for illustrative and descriptive purposes only. While the processes and compositions are described as using specific a specific order of individual steps or specific materials, it is appreciated that steps or materials may be interchangeable such that the description of the invention may include multiple steps or parts arranged in many ways as is readily appreciated by one of skill in the art.

Reference will now be made in detail to various embodiments of the instantly-disclosed antipathogenic polypeptides, nucleic acids that encode such antipathogenic polypeptides, expression cassettes, plasmids, expression vectors, recombinant viruses, or cells comprising such nucleic acids, and antipathogenic compositions and formulations. As described, these various novel compositions find use in methods of treating a product, including an agricultural product, from a pathogen, such as fungi and algae.

The terminology used herein is for describing particular embodiments/aspects only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Antipathogenic Polypeptides and Nucleic Acids

In aspects, the present disclosure provides antipathogenic polypeptides, as well as nucleic acids (e.g., DNA or RNA) encoding one or more polypeptides of the present disclosure. The instantly-disclosed antipathogenic polypeptides display antipathogenic activity, antifungal activity (i.e., act as fungicides), antialgal activity (i.e., act as algaecides), and/or enzymatic activity against chitin (i.e., degrade chitin) and/or polyglucuronic acid (i.e., degrade the polyglucuronic acid). In aspects, the instantly-disclosed polypeptides display antifungal activity against a wide variety of fungi, including but not limited to: *Botrytis* spp.; *Mucor, Cladosporium* spp.; *Fusarium* spp.; *Talaromyces* spp.; *Rhizopus* spp.; *Verticillium* spp.; Chaetomeum *Issatchenkia* spp.; Gelainspora spp.; *Macrophomina* spp.; Anthracnose spp.; *Podosphaera* spp.; *Sphaerotheca* spp.; *Penicillium* spp.; *Aspergillus* spp.; *Uncinula* spp.; *Guignardia* spp.; *Fusicoccum* spp.; Paecilomyes spp.; *Byssochlamys* spp.; and Mucoraceae spp. In aspects, these polypeptides display antialgal activity against a wide variety of harmful algae and harmful algal blooms. As such, these antipathogenic polypeptides, as well as nucleic acids (e.g., DNA or RNA) encoding one or more polypeptides, can be used in protecting/treating products, including but not limited to agricultural products and water bodies (including drinking water), from pathogens, including fungi and algae, as well as generating pathogen-resistant products (particularly fungi and algae-resistant products).

In aspects, the present disclosure is directed to antipathogenic polypeptides having a an amino acid set forth in SEQ ID NO: 1, SEQ ID NO: 2, SEQ ID NO: 3, SEQ ID NO: 4, SEQ ID NO: 5, or SEQ ID NO: 6, and variants and fragments thereof. In some aspects, the present disclosure is directed to a polypeptide having antipathogenic activity, said polypeptide comprising an amino acid sequence having at least 75%, 80%, 85%, 90%, or 95% homology to SEQ ID NO: 1, SEQ ID NO: 2, SEQ ID NO: 3, SEQ ID NO: 4, SEQ ID NO: 5, or SEQ ID NO: 6, and variants and fragments thereof. In aspects of the above-referenced polypeptides polypeptide having antifungal and/or antialgal activity. In aspects of the above-described polypeptides, the polypeptides may be isolated, synthetic, or recombinant.

In some aspects, the present disclosure is directed to a polypeptide having antipathogenic activity, said polypeptide comprising an amino acid sequence of SEQ ID NO: 2, and variants and fragments thereof. In aspects, the present disclosure is directed to a polypeptide having antipathogenic activity, said polypeptide comprising an amino acid sequence having at least 75%, 80%, 85%, 90%, or 95% homology to SEQ ID NO: 2, and variants and fragments thereof. In further aspects, the present disclosure is directed to an antipathogenic polypeptide having antipathogenic activity, said polypeptide comprising an amino acid sequence having at least 75%, 80%, 85%, 90%, or 95% homology to SEQ ID NO: 2 and further comprising a phenylalanine at amino acid position 152, and variants and fragments thereof. In additional aspects, the present disclosure is directed to a polypeptide having antifungal activity, said polypeptide comprising an amino acid sequence of SEQ ID NO: 2, and variants and fragments thereof. In some aspects, the present disclosure is directed to a polypeptide having antifungal activity, said polypeptide comprising an amino acid sequence having at least 75%, 80%, 85%, 90%, or 95% homology to SEQ ID NO: 2, and variants and fragments thereof. In aspects, the present disclosure is directed to a polypeptide having antifungal activity, said polypeptide comprising an amino acid sequence of SEQ ID NO: 2 and further comprising a phenylalanine at amino acid position 152, and variants and fragments thereof. In even further aspects, the present disclosure is directed to a polypeptide having antifungal activity, said polypeptide comprising an amino acid sequence having at least 75%, 80%, 85%, 90%, or 95% homology to SEQ ID NO: 2 and further comprising a phenylalanine at amino acid position 152, and variants and fragments thereof. In aspects of the above-described polypeptides, the polypeptides may be isolated, synthetic, or recombinant. In aspects, these polypeptides display enzymatic activity against chitin. In aspects, these polypeptides display antifungal activity against a wide variety of fungi, including but not limited to: *Botrytis* spp.; *Mucor, Cladosporium* spp.; *Fusarium* spp.; *Talaromyces* spp.; *Rhizopus* spp.; *Verticillium* spp.; Chaetomeum *Issatchenkia* spp.; Gelainspora spp.; *Macrophomina* spp.; Anthracnose spp.; *Podosphaera* spp.; *Sphaerotheca* spp.; *Penicillium* spp.; *Aspergillus* spp.; *Uncinula* spp.; *Guignardia* spp.; *Fusicoccum* spp.; Paecilomyes spp.; *Byssochlamys* spp.; and Mucoraceae spp. In aspects, the present disclosure is directed to a polynucleotide (e.g., DNA or RNA) encoding one or more such polypeptides. In aspects of the instantly-disclosed polynucleotides, the polynucleotides may be isolated, synthetic, or recombinant.

In some aspects, the present disclosure is directed to a polypeptide having antipathogenic activity, said polypeptide comprising an amino acid sequence of SEQ ID NO: 3, and variants and fragments thereof. In aspects, the present disclosure is directed to a polypeptide having antipathogenic activity, said polypeptide comprising an amino acid sequence having at least 75%, 80%, 85%, 90%, or 95% homology to SEQ ID NO: 3, and variants and fragments thereof. In further aspects, the present disclosure is directed to an antipathogenic polypeptide having antipathogenic activity, said polypeptide comprising an amino acid sequence having at least 75%, 80%, 85%, 90%, or 95% homology to SEQ ID NO: 3 and further comprising a phenylalanine at amino acid position 202, and variants and fragments thereof. In additional aspects, the present disclosure is directed to a polypeptide having antifungal and/or antialgal activity, said polypeptide comprising an amino acid sequence of SEQ ID NO: 3, and variants and fragments thereof. In some aspects, the present disclosure is directed to a polypeptide having antifungal and/or antialgal activity, said polypeptide comprising an amino acid sequence having at least 75%, 80%, 85%, 90%, or 95% homology to SEQ ID NO: 3, and variants and fragments thereof. In aspects, the present disclosure is directed to a polypeptide having antifungal and/or antialgal activity, said polypeptide comprising an amino acid sequence of SEQ ID NO: 3 and further comprising a phenylalanine at amino acid position 202, and variants and fragments thereof. In even further aspects, the present disclosure is directed to a polypeptide having antifungal and/or antialgal activity, said polypeptide comprising an amino acid sequence having at least 75%, 80%, 85%, 90%, or 95% homology to SEQ ID NO: 3 and further comprising a phenylalanine at amino acid position 202, and variants and fragments thereof. In aspects of the above-described polypeptides, the polypeptides may be isolated, synthetic, or recombinant. In aspects, these polypeptides display enzymatic activity against chitin and/or polyglucuronic acid. In aspects, these polypeptides display antifungal activity against a wide variety of fungi, including but not limited to: *Botrytis* spp.; *Mucor, Cladosporium* spp.; *Fusarium* spp.; *Talaromyces* spp.; *Rhizopus* spp.; *Verticillium* spp.; Chaetomeum *Issatchenkia* spp.; Gelainspora spp.; *Macrophomina* spp.; Anthracnose spp.; *Podosphaera* spp.; *Sphaerotheca* spp.; *Penicillium* spp.; *Aspergillus* spp.; *Uncinula* spp.; *Guignardia* spp.; *Fusicoccum* spp.; Paecilomyes spp.; *Byssochlamys* spp.; and Mucoraceae spp. In aspects, the present disclosure is directed to a polynucleotide (e.g., DNA or RNA) encoding one or more such polypeptides. In aspects of the instantly-disclosed polynucleotides, the polynucleotides may be isolated, synthetic, or recombinant.

In some aspects, the present disclosure is directed to a polypeptide having antipathogenic activity, said polypeptide comprising an amino acid sequence of SEQ ID NO: 4, and variants and fragments thereof. In aspects, the present disclosure is directed to a polypeptide having antipathogenic activity, said polypeptide comprising an amino acid sequence having at least 75%, 80%, 85%, 90%, or 95% homology to SEQ ID NO: 4, and variants and fragments thereof. In further aspects, the present disclosure is directed to an antipathogenic polypeptide having antipathogenic activity, said polypeptide comprising an amino acid sequence having at least 75%, 80%, 85%, 90%, or 95% homology to SEQ ID NO: 4 and further comprising a phenylalanine at amino acid position 202 and a phenylalanine at amino acid position 208, and variants and fragments thereof. In additional aspects, the present disclosure is directed to a polypeptide having antifungal and/or antialgal activity, said polypeptide comprising an amino acid sequence of SEQ ID NO: 4, and variants and fragments thereof. In some aspects, the present disclosure is directed to a polypeptide having antifungal and/or antialgal activity, said polypeptide comprising an amino acid sequence having at least 75%, 80%, 85%, 90%, or 95% homology to SEQ ID NO: 4, and variants and fragments thereof. In aspects, the present disclosure is directed to a polypeptide having antifungal and/or antialgal activity, said polypeptide comprising an amino acid sequence of SEQ ID NO: 4 and further comprising a phenylalanine at amino acid position 202 and a phenylalanine at amino acid position 208, and variants and fragments thereof. In even further aspects, the present disclosure is directed to a polypeptide having antifungal and/or antialgal activity, said polypeptide comprising an amino acid sequence having at least 75%, 80%, 85%, 90%, or 95% homology to SEQ ID NO: 4 and further comprising a phenylalanine at amino acid position 202 and a phenylalanine at amino acid position 208, and variants and fragments thereof. In aspects of the above-described polypeptides, the polypeptides may be isolated, synthetic, or recombinant. In aspects, these polypeptides display enzymatic activity against chitin and/or polyglucuronic acid. In aspects, these polypeptides display antifungal activity against a wide variety of fungi, including but not limited to: *Botrytis* spp.; *Mucor, Cladosporium* spp.; *Fusarium* spp.; *Talaromyces* spp.; *Rhizopus* spp.; *Verticillium* spp.; Chaetomeum *Issatchenkia* spp.; Gelainspora spp.; *Macrophomina* spp.; Anthracnose spp.; *Podosphaera* spp.; *Sphaerotheca* spp.; *Penicillium* spp.; *Aspergillus* spp.; *Uncinula* spp.; *Guignardia* spp.; *Fusicoccum* spp.; Paecilomyes spp.; *Byssochlamys* spp.; and Mucoraceae spp. In aspects, the present disclosure is directed to a polynucleotide (e.g., DNA or RNA) encoding one or more such polypeptides. In aspects of the instantly-disclosed polynucleotides, the polynucleotides may be isolated, synthetic, or recombinant.

In some aspects, the present disclosure is directed to a polypeptide having antipathogenic activity, said polypeptide comprising an amino acid sequence having at least 75%, 80%, 85%, 90%, or 95% homology to SEQ ID NO: 5, and variants and fragments thereof. In further aspects, the present disclosure is directed to an antipathogenic polypeptide having antipathogenic activity, said polypeptide comprising an amino acid sequence having at least 75%, 80%, 85%, 90%, or 95% homology to SEQ ID NO: 5 and further comprising an alanine at amino acid position 153, and variants and fragments thereof. In additional aspects, the present disclosure is directed to a polypeptide having antifungal and/or antialgal activity, said polypeptide comprising an amino acid sequence selected from the group consisting of SEQ ID NO: 5, and variants and fragments thereof. In some aspects, the present disclosure is directed to a polypeptide having antifungal and/or antialgal activity, said polypeptide comprising an amino acid sequence having at least 75%, 80%, 85%, 90%, or 95% homology to SEQ ID NO: 5, and variants and fragments thereof. In aspects, the present disclosure is directed to a polypeptide having antifungal activity, said polypeptide comprising an amino acid sequence selected from the group consisting of SEQ ID NO: 5 and further comprising an alanine at amino acid position 153, and variants and fragments thereof. In even further aspects, the present disclosure is directed to a polypeptide having antifungal activity, said polypeptide comprising an amino acid sequence having at least 75%, 80%, 85%, 90%, or 95% homology to SEQ ID NO: 5 and further comprising a alanine at amino acid position 153, and variants and fragments thereof. In aspects of the above-described polypeptides, the polypeptides may be isolated, synthetic, or recombinant. In aspects, these polypeptides display enzymatic activity against chitin. In aspects, these polypeptides display antifungal activity against a wide variety of fungi, including but not limited to: *Botrytis* spp.; *Mucor, Cladosporium* spp.; *Fusarium* spp.; *Talaromyces* spp.; *Rhizopus* spp.; *Verticillium* spp.; Chaetomeum *Issatchenkia* spp.; Gelainspora spp.; *Macrophomina* spp.; Anthracnose spp.; *Podosphaera* spp.; *Sphaerotheca* spp.; *Penicillium* spp.; *Aspergillus* spp.; *Uncinula* spp.; *Guignardia* spp.; *Fusicoccum* spp.; Paecilomyes spp.; *Byssochlamys* spp.; and Mucoraceae spp. In aspects, the present disclosure is directed to a polynucleotide (e.g., DNA or RNA) encoding one or more such polypeptides. In aspects of the instantly-disclosed polynucleotides, the polynucleotides may be isolated, synthetic, or recombinant.

In some aspects, the present disclosure is directed to a polypeptide having antipathogenic activity, said polypeptide comprising an amino acid sequence having at least 75%, 80%, 85%, 90%, or 95% homology to SEQ ID NO: 6, and variants and fragments thereof. In further aspects, the present disclosure is directed to an antipathogenic polypeptide having antipathogenic activity, said polypeptide comprising an amino acid sequence having at least 75%, 80%, 85%, 90%, or 95% homology to SEQ ID NO: 6 and further comprising a phenylalanine at amino acid position 455, and variants and fragments thereof. In additional aspects, the present disclosure is directed to a polypeptide having antifungal and/or antialgal activity, said polypeptide comprising an amino acid sequence selected from the group consisting of SEQ ID NO: 6, and variants and fragments thereof. In some aspects, the present disclosure is directed to a polypeptide having antifungal and/or antialgal activity, said polypeptide comprising an amino acid sequence having at least 75%, 80%, 85%, 90%, or 95% homology to SEQ ID NO: 6, and variants and fragments thereof. In aspects, the present disclosure is directed to a polypeptide having antifungal activity, said polypeptide comprising an amino acid sequence selected from the group consisting of SEQ ID NO: 6 and further comprising a phenylalanine at amino acid position 455, and variants and fragments thereof. In even further aspects, the present disclosure is directed to a polypeptide having antifungal activity, said polypeptide comprising an amino acid sequence having at least 75%, 80%, 85%, 90%, or 95% homology to SEQ ID NO: 6 and further comprising a phenylalanine at amino acid position 455, and variants and fragments thereof. In aspects of the above-described polypeptides, the polypeptides may be isolated, synthetic, or recombinant. In aspects, these polypeptides display enzymatic activity against chitin and/or polyglucuronic acid. In aspects, these polypeptides display antifungal activity against a wide variety of fungi, including but not limited to: *Botrytis* spp.; *Mucor, Cladosporium* spp.; *Fusarium* spp.; *Talaromyces* spp.; *Rhizopus* spp.; *Verticillium* spp.; Chaetomeum *Issatchenkia* spp.; Gelainspora spp.; *Macrophomina* spp.; Anthracnose spp.; *Podosphaera* spp.; *Sphaerotheca* spp.; *Penicillium* spp.; *Aspergillus* spp.; *Uncinula* spp.; *Guignardia* spp.; *Fusicoccum* spp.; Paecilomyes spp.; *Byssochlamys* spp.; and Mucoraceae spp. In aspects, the present disclosure is directed to a polynucleotide (e.g., DNA or RNA) encoding one or more such polypeptides. In aspects of the instantly-disclosed polynucleotides, the polynucleotide may be isolated, synthetic, or recombinant.

In some aspects, a genetically modified polysaccharide lyase polypeptide having antipathogenic activity is provided, said polypeptide comprising an amino acid sequence having at least 75%, 80%, 85%, 90%, or 95% homology to SEQ ID NO: 1 and comprising the mutation W152F, and variants and fragments thereof. The notation for the specific genetic modification, as well as similar notations for genetic modifications disclosed throughout the instant specification, adhere to industry standard wherein the amino acid modifications are defined as the original single letter amino acid code, followed by the amino acid position, followed by the new amino acid single letter code. In aspects, these genetically modified polysaccharide lyase polypeptides may be isolated, synthetic, or recombinant. In aspects, the amino acid sequence of the genetically modified polysaccharide lyase polypeptides is obtained from *Stenotrophomonas maltophilia* (Smlt2602; UniProt ID B2FSW8). In aspects, these genetically modified polysaccharide lyase polypeptides display enzymatic activity against chitin. In aspects, these genetically modified polysaccharide lyase polypeptides display antifungal activity. In aspects, these polypeptides display antifungal activity against a wide variety of fungi, including but not limited to: *Botrytis* spp.; *Mucor, Cladosporium* spp.; *Fusarium* spp.; *Talaromyces* spp.; *Rhizopus* spp.; *Verticillium* spp.; Chaetomeum *Issatchenkia* spp.; Gelainspora spp.; *Macrophomina* spp.; Anthracnose spp.; *Podosphaera* spp.; *Sphaerotheca* spp.; *Penicillium* spp.; *Aspergillus* spp.; *Uncinula* spp.; *Guignardia* spp.; *Fusicoccum* spp.; Paecilomyes spp.; *Byssochlamys* spp.; and Mucoraceae spp. In aspects, the present disclosure is directed to a polynucleotide (e.g., DNA or RNA) encoding one or more such genetically modified polysaccharide lyase polypeptides. In aspects of the instantly-disclosed polynucleotides, the polynucleotides may be isolated, synthetic, or recombinant.

In aspects, a genetically modified polysaccharide lyase polypeptide having antipathogenic activity is provided, said polypeptide comprising an amino acid sequence having at least 75%, 80%, 85%, 90%, or 95% homology to SEQ ID NO: 1 and comprising the mutation Y202F. In aspects, these genetically modified polysaccharide lyase polypeptides may be isolated, synthetic, or recombinant. In aspects, the amino acid sequence of the genetically modified polysaccharide lyase polypeptides is obtained from *Stenotrophomonas maltophilia* (Smlt2602; UniProt ID B2FSW8). In aspects, these genetically modified polysaccharide lyase polypeptides display enzymatic activity against chitin and/or polyglucuronic acid. In aspects, these genetically modified polysaccharide lyase polypeptides display antifungal and/or antialgal activity. In aspects, these polypeptides display antifungal activity against a wide variety of fungi, including but not limited to: *Botrytis* spp.; *Mucor, Cladosporium* spp.; *Fusarium* spp.; *Talaromyces* spp.; *Rhizopus* spp.; *Verticillium* spp.; Chaetomeum *Issatchenkia* spp.; Gelainspora spp.; *Macrophomina* spp.; Anthracnose spp.; *Podosphaera* spp.; *Sphaerotheca* spp.; *Penicillium* spp.; *Aspergillus* spp.; *Uncinula* spp.; *Guignardia* spp.; *Fusicoccum* spp.; Paecilomyes spp.; *Byssochlamys* spp.; and Mucoraceae spp. In aspects, the present disclosure is directed to a polynucleotide (e.g., DNA or RNA) encoding one or more such genetically modified polysaccharide lyase polypeptides. In aspects of the instantly-disclosed polynucleotides, the polynucleotides may be isolated, synthetic, or recombinant.

In additional aspects, a genetically modified polysaccharide lyase polypeptide having antipathogenic activity is provided, said polypeptide comprising an amino acid sequence having at least 75%, 80%, 85%, 90%, or 95% homology to SEQ ID NO: 1 and comprising the mutations Y202F and H208F. In aspects, these genetically modified polysaccharide lyase polypeptides may be isolated, synthetic, or recombinant. In aspects, the amino acid sequence of the genetically modified polysaccharide lyase polypeptides is obtained from *Stenotrophomonas maltophilia* (Smlt2602; UniProt ID B2FSW8). In aspects, these genetically modified polysaccharide lyase polypeptides display enzymatic activity against chitin and/or polyglucuronic acid. In aspects, these genetically modified polysaccharide lyase polypeptides display antifungal and/or antialgal activity. In aspects, these polypeptides display antifungal activity against a wide variety of fungi, including but not limited to: *Botrytis* spp.; *Mucor, Cladosporium* spp.; *Fusarium* spp.; *Talaromyces* spp.; *Rhizopus* spp.; *Verticillium* spp.; Chaetomeum *Issatchenkia* spp.; Gelainspora spp.; *Macro-*

*phomina* spp.; Anthracnose spp.; *Podosphaera* spp.; *Sphaerotheca* spp.; *Penicillium* spp.; *Aspergillus* spp.; *Uncinula* spp.; *Guignardia* spp.; *Fusicoccum* spp.; Paecilomyes spp.; *Byssochlamys* spp.; and Mucoraceae spp. In aspects, the present disclosure is directed to a polynucleotide (e.g., DNA or RNA) encoding one or more such genetically modified polysaccharide lyase polypeptides. In aspects of the instantly-disclosed polynucleotides, the polynucleotides may be isolated, synthetic, or recombinant.

In further aspects, a genetically modified polysaccharide lyase polypeptide having antipathogenic is provided, said polypeptide comprising an amino acid sequence having at least 75%, 80%, 85%, 90%, or 95% homology to SEQ ID NO: 1 and comprising the mutation Q153A. In aspects, these genetically modified polysaccharide lyase polypeptides may be isolated, synthetic, or recombinant. In aspects, the amino acid sequence of the genetically modified polysaccharide lyase polypeptides is obtained from *Stenotrophomonas maltophilia* (Smlt2602; UniProt ID B2FSW8). In aspects, these genetically modified polysaccharide lyase polypeptides display enzymatic activity against chitin. In aspects, these genetically modified polysaccharide lyase polypeptides display antifungal activity. In aspects, these polypeptides display antifungal activity against a wide variety of fungi, including but not limited to: *Botrytis* spp.; *Mucor, Cladosporium* spp.; *Fusarium* spp.; *Talaromyces* spp.; *Rhizopus* spp.; *Verticillium* spp.; Chaetomeum *Issatchenkia* spp.; Gelainspora spp.; *Macrophomina* spp.; Anthracnose spp.; *Podosphaera* spp.; *Sphaerotheca* spp.; *Penicillium* spp.; *Aspergillus* spp.; *Uncinula* spp.; *Guignardia* spp.; *Fusicoccum* spp.; Paecilomyes spp.; *Byssochlamys* spp.; and Mucoraceae spp. In aspects, the present disclosure is directed to a polynucleotide (e.g., DNA or RNA) encoding one or more such genetically modified polysaccharide lyase polypeptides. In aspects of the instantly-disclosed polynucleotides, the polynucleotides may be isolated, synthetic, or recombinant.

In aspects, a genetically modified polysaccharide lyase polypeptide having antipathogenic is provided, said polypeptide comprising an amino acid sequence having at least 75%, 80%, 85%, 90%, or 95% homology to SEQ ID NO: 1 and comprising the mutation Y455F. In aspects, these genetically modified polysaccharide lyase polypeptides may be isolated, synthetic, or recombinant. In aspects, the amino acid sequence of the genetically modified polysaccharide lyase polypeptides is obtained from *Stenotrophomonas maltophilia* (Smlt2602; UniProt ID B2FSW8). In aspects, these genetically modified polysaccharide lyase polypeptides display enzymatic activity against chitin. In aspects, these genetically modified polysaccharide lyase polypeptides display antifungal activity. In aspects, these polypeptides display antifungal activity against a wide variety of fungi, including but not limited to: *Botrytis* spp.; *Mucor, Cladosporium* spp.; *Fusarium* spp.; *Talaromyces* spp.; *Rhizopus* spp.; *Verticillium* spp.; Chaetomeum *Issatchenkia* spp.; Gelainspora spp.; *Macrophomina* spp.; Anthracnose spp.; *Podosphaera* spp.; *Sphaerotheca* spp.; *Penicillium* spp.; *Aspergillus* spp.; *Uncinula* spp.; *Guignardia* spp.; *Fusicoccum* spp.; Paecilomyes spp.; *Byssochlamys* spp.; and Mucoraceae spp. In aspects, the present disclosure is directed to a polynucleotide (e.g., DNA or RNA) encoding one or more such genetically modified polysaccharide lyase polypeptides. In aspects of the instantly-disclosed polynucleotides, the polynucleotides may be isolated, synthetic, or recombinant.

In aspects, the present disclosure is directed to a polynucleotide (e.g., DNA or RNA) encoding one or more polypeptides of the present disclosure. In aspects of the instantly-disclosed polynucleotides, the polynucleotides may be isolated, synthetic, or recombinant. In aspects, the polynucleotides further comprises, or is contained within, an expression cassette, a plasmid, and expression vector, or recombinant virus, wherein optionally the polynucleotides, or the expression cassette, plasmid, expression vector, or recombinant virus is contained within a cell, optionally a non-human cell, such as a plant cell or a microbial host, and optionally the cell is transformed with the polynucleotides, or the expression cassette, plasmid, expression vector, or recombinant virus of the instant disclosure. In aspects, cells are transduced, transfected, or otherwise engineered to contain within one or more of the polynucleotides, or the expression cassette, plasmid, expression vector, or recombinant virus as disclosed herein. In aspects, the cell can be a plant cell, bacterial or microbial cell, insect cell, or yeast cell. In aspects, the nucleic acid molecules of the present disclosure can be inserted into vectors and used, for example, as expression vectors or gene therapy vectors.

"Antipathogenic", "antipathogenic polypeptides", and "antipathogenic compositions" are intended to mean that the polypeptides and compositions of the instant disclosure have antipathogenic activity and thus are capable of suppressing, controlling, and/or killing the invading pathogenic organism. An antipathogenic polypeptide of the instant disclosure will reduce the disease symptoms resulting from pathogen challenge by at least about 5% to about 50%, at least about 10% to about 60%, at least about 30% to about 70%, at least about 40% to about 80%, or at least about 50% to about 90% or greater, including any value or range therebetween. In particular embodiments, the antipathogenic activity exhibited by the polypeptides of the invention is antifungal activity. As used herein, "antifungal activity" or the like refers to the ability to suppress, control, and/or kill the invading fungal pathogen. Likewise, "fungal resistance" refers to enhanced tolerance to a fungal pathogen when compared to that of an untreated or wild type product, e.g., an agricultural product. Resistance may vary from a slight increase in tolerance to the effects of the fungal pathogen (e.g., partial inhibition) to total resistance such that the plant is unaffected by the presence of the fungal pathogen. An increased level of resistance against a particular fungal pathogen or against a wider spectrum of fungal pathogens may both constitute antifungal activity or improved fungal resistance. Similarly, "antialgal activity" or the like refers to the ability to suppress, control, and/or kill the invading algae pathogen. Likewise, "algae resistance" refers to enhanced tolerance to algae pathogens when compared to that of an untreated or wild type product, e.g., an agricultural product. Resistance may vary from a slight increase in tolerance to the effects of an alga pathogen (e.g., partial inhibition) to total resistance such that the product, e.g., an agricultural product, is unaffected by the presence of an alga pathogen. An increased level of resistance against a particular alga pathogen or against a wider spectrum of algae pathogens may both constitute antialgal activity or improved algal resistance.

The terms "polypeptide," "peptide," and "protein" are used interchangeably herein to refer to a polymer of amino acid residues. The terms may apply to amino acid polymers in which one or more amino acid residues is an artificial chemical analogue of a corresponding naturally occurring amino acid, as well as to naturally occurring amino acid polymers.

The terms "polynucleotide" and "nucleic acid sequence" are used interchangeably to refer to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides. The term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, and the like. As used herein, the terms "encoding" or "encoded" when used in the context of a specified polynucleotide mean that the polynucleotide comprises the requisite information to direct translation of the polynucleotide sequence into a specified polypeptide. The information by which a polypeptide is encoded is specified by the use of codons. A polynucleotide encoding a polypeptide may comprise non-translated sequences (e.g., introns) within translated regions of the nucleic acid or may lack such intervening non-translated sequences (e.g., as in cDNA).

As used herein, a polypeptide or polynucleotide is said to be "isolated" or "purified" when it is substantially free of cellular material when it is isolated from recombinant and non-recombinant cells, or free of chemical precursors or other chemicals when it is chemically synthesized. As such, an isolated or purified polypeptide or polynucleotide is substantially free of other cellular material, or culture medium when produced by recombinant techniques, or substantially free of chemical precursors or other chemicals when chemically synthesized. Optimally, an "isolated" n is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide or polynucleotide that is substantially free of cellular material includes preparations of polypeptides having less than about 30%, 20%, 10%, 5%, 1%, or any value or range therebetween (by dry weight) of other proteins (e.g., contaminating proteins). When the polypeptides of the invention or biologically active portion thereof are recombinantly produced, optimally culture medium represents less than about 30%, 20%, 10%, 5%, 1%, or any value or range therebetween (by dry weight) of chemical precursors or non-protein-of-interest chemicals that are involved in the polypeptide or polynucleotide synthesis.

As used herein, two polypeptides (or a region of the proteins) are substantially homologous when the amino acid sequences have a certain percentage or more identity, e.g., at least about 50% 60%, 65%, 70%, 75%, 80%, 85%, 90%, 91%, 92%, 93%, 94%, 95%, 96%, 97%, 98%, or 99% identity. Percent homology can be determined as is known in the art. For example, to determine the percent identity of two amino acid sequences, the sequences are aligned for optimal comparison purposes (e.g., gaps can be introduced in one or both of a first and a second amino acid sequence for optimal alignment and non-homologous sequences can be disregarded for comparison purposes). The amino acid residues at corresponding amino acid positions are then compared. When a position in the first sequence is occupied by the same amino acid residue as the corresponding position in the second sequence, then the molecules are identical at that position (as used herein amino acid "identity" is equivalent to amino acid "homology"). As is known in the art, the percent identity between the two sequences is a function of the number of identical positions shared by the sequences, taking into account the number of gaps, and the length of each gap, which need to be introduced for optimal alignment of the two sequences. Sequence homology for polypeptides is typically measured using sequence analysis software.

When homologous is used in reference to polypeptides, it is recognized that residue positions that are not identical can often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are known to those of skill in the art. The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

In embodiments, amino acid residues which are not believed to be essential for the functioning of the instantly-disclosed polypeptides may be substituted either conservatively or non-conservatively, and such amino acid substitutions would likely not significantly diminish the functional properties of the polypeptides. In embodiments, most conservative and nonconservative amino acid substitutions for certain amino acid residues which are believed to form the active site of the polypeptides (e.g., residues 143, 156, 201, 204, 206, 207, 208, 211, 252, 257, 258, 263, 264, 267, 319, 328, 418, 439, 443, 444, 446, 488, and 669 of SEQ ID NOs: 1-6), other than those specific amino acid substitutions described herein, will likely diminish the functional properties (e.g., the antipathogenic activity, antifungal activity, antialgal activity, and/or enzymatic activity against chitin and/or polyglucuronic acid) of the polypeptides. In embodiments, most conservative and nonconservative amino acid substitutions for certain amino acid residues which are believed to form the active site of the instantly-disclosed polypeptides (e.g., residues 96, 155, 260, 266, 321, 420, 421, 459, 460, 484, 490, 664, 667, and 670 of SEQ ID NOs: 1-6), other than those specific amino acid substitutions disclosed herein, will likely not diminish the functional properties (e.g., the antipathogenic activity, antifungal activity, antialgal activity, and/or enzymatic activity against chitin and/or polyglucuronic acid) of the polypeptides. In embodiments, most conservative and nonconservative amino acid substitutions for certain amino acid residues in the catalytic domain of the instantly-disclosed polypeptides (e.g., residues 143, 156, 201, 204, 206, 207, 208, 211, 252, 257, 258, 263, 264, 267, 319, 328, 418, 439, 443, 444, 446, 488, and 669 of SEQ ID NOs: 1-6), other than those specific amino acid substitutions described herein, will likely diminish the functional properties (e.g., the antipathogenic activity, antifungal activity, antialgal activity, and/or enzymatic activity against chitin and/or polyglucuronic acid) of the polypeptides. In embodiments, most conservative and nonconservative amino acid substitutions for all other amino acid residues in the catalytic domain of the instantly-disclosed polypeptides polypeptides (e.g., residues 96, 155, 260, 266, 321, 420, 421, 459, 460, 484, 490, 664, 667, and 670 of SEQ ID NOs: 1-6), other than those specific amino acid substitutions described herein, will likely not diminish the functional properties (e.g., the antipathogenic activity, antifungal activity, antialgal activity, and/or enzymatic activity against chitin and/or polyglucuronic acid) of the polypeptides. It is believed that the instantly-disclosed polypeptides having the described modifications/substitutions would confer the desired activity (e.g., the antipathogenic activity, antifungal activity, antialgal activity, and/or enzymatic activity against chitin and/or polyglucuronic acid). Stated another way, it is believed that the amino acid substitutions described herein would not significantly diminish the functional properties of the instantly-disclosed polypeptides (e.g., the antipathogenic activity, antifungal activity, antialgal activity, and/or enzymatic activity against chitin and/or polyglucuronic acid).

Fragments and variants of the disclosed polypeptides and polynucleotides are also encompassed by the present invention. "Fragment" is intended to mean a portion of the polypeptide or polynucleotide. Fragments of a polypeptide or a nucleotide sequence as disclosed herein may encode polypeptide fragments that retain the biological activity of the polypeptides of the instant disclosure, and hence have antipathogenic activity, antifungal activity, antialgal activity, and/or enzymatic activity against chitin and/or polyglucuronic acid. In aspects, the present disclosure also encompasses fragments of the variants of the polypeptides and polynucleotides described herein.

"Variants" is intended to mean substantially similar sequences. A "variant" polypeptide is intended to mean a polypeptide derived from the instantly-disclosed polypeptides of the current invention by deletion or addition of one or more amino acids at one or more internal sites in the native protein and/or substitution of one or more amino acids at one or more sites in the native protein. Variant polypeptides encompassed by the present invention are biologically active, that is they continue to possess the desired biological activity the polypeptides of the instant-disclosure, that is, antipathogenic activity, antifungal activity, antialgal activity, and/or enzymatic activity against chitin and/or polyglucuronic acid as described herein. Such variants may result from, for example, genetic polymorphism or from human manipulation. Biologically active variants will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the polypeptides of the invention as determined by sequence alignment programs and parameters described elsewhere herein. A biologically active variant of a polypeptide of the invention may differ from that polypeptide by as few as 1-15 amino acid residues, as few as 1-10, such as 6-10, as few as 5, as few as 4, 3, 2, or even 1 amino acid residue.

The polypeptides of the instant disclosure may be altered in various ways including amino acid substitutions, deletions, truncations, and insertions. Methods for such manipulations are generally known in the art. For example, amino acid sequence variants and fragments of the instantly-disclosed polypeptides can be prepared by mutations in the DNA. Methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be optimal. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr. Guidance concerning which amino acid changes are likely to be phenotypically silent are found (Bowie J U et al., (1990), Science, 247(4948):130610, which is herein incorporated by reference in its entirety). For the purposes of the present disclosure, polypeptides can include, for example, modified forms of naturally occurring amino acids such as D-stereoisomers, non-naturally occurring amino acids; amino acid analogs; and mimetics.

Polypeptides of the invention can be produced either from a nucleic acid disclosed herein, or by the use of standard molecular biology techniques, such as recombinant techniques, mutagenesis, or other known means in the art. An isolated polypeptide can be purified from cells that naturally express it, purified from cells that have been altered to express it (recombinant), or synthesized using known protein synthesis techniques. In aspects, a polypeptides of the instant disclosure are produced by recombinant DNA or RNA techniques. In aspects, a polypeptide of the invention can be produced by expression of a recombinant nucleic acid of the invention in an appropriate host cell. For example, a nucleic acid molecule encoding the polypeptide is cloned into an expression cassette or expression vector, the expression cassette or expression vector introduced into a host cell and the polypeptide expressed in the host cell. The polypeptide can then be isolated from the cells by an appropriate purification scheme using standard protein purification techniques. Alternatively a polypeptide can be produced by a combination of ex vivo procedures, such as protease digestion and purification. Further, polypeptides of the invention can be produced using site-directed mutagenesis techniques, or other mutagenesis techniques known in the art (see e.g., James A. Brannigan and Anthony J. Wilkinson., 2002, Protein engineering 20 years on. Nature Reviews Molecular Cell Biology 3, 964-970; Turanli-Yildiz B. et al., 2012, Protein Engineering Methods and Applications, intechopen.com, which are herein incorporated by reference in their entirety).

For polynucleotides, a "variant" comprises a deletion and/or addition of one or more nucleotides at one or more internal sites within the polynucleotide sequences of the instant disclosure and/or a substitution of one or more nucleotides at one or more sites in the polynucleotide sequences of the instant disclosure. One of skill in the art will recognize that variants of the polynucleotides of the invention will be constructed such that the open reading frame is maintained. For polynucleotides, conservative variants include those sequences that, because of the degeneracy of the genetic code, encode the amino acid sequence of one of the polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a polynucleotide having the desired activity of the invention (i.e., encoding a polypeptide that possesses the desired biological activity, that is, antipathogenic activity, antifungal activity, antialgal activity, and/or enzymatic activity against chitin and/or polyglucuronic acid as described herein). Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptides of SEQ ID NOs: 1-6 (including the noted mutations/modifications) are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

The polynucleotides provided herein (whether RNA, DNA, expression cassettes, vectors, viruses or hybrids thereof) that encode in whole or in part one or more polypeptides of the present disclosure can be isolated from a variety of sources, genetically engineered, amplified, synthetically produced, and/or expressed/generated recombinantly. Recombinant polypeptides generated from these nucleic acids can be individually isolated or cloned and tested for a desired activity. Any recombinant expression system can be used, including e.g. in vitro, bacterial, fungal, mammalian, yeast, insect or plant cell expression systems. In aspects polynucleotides provided herein are synthesized in vitro by well-known chemical synthesis techniques (as described in, e.g., Adams (1983) J. Am. Chem. Soc. 105: 661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066, all of which are herein incorporated by reference in their entirety). Further, techniques for the manipulation of polynucleotides provided herein, such as, e.g., subcloning, labeling probes (e.g., random-primer labeling using Klenow polymerase, nick translation, amplification), sequencing, hybridization and the like are well described in the scientific and patent literature (see, e.g., Sambrook, ed., Molecular Cloning: A Laboratory Manual (2ND ED.), Vols. 1-3, Cold Spring Harbor Laboratory, (1989); Current Protocols In Molecular Biology, Ausubel, ed. John Wiley & Sons, Inc., New York (1997); Laboratory Techniques In Biochemistry And Molecular Biology: Hybridization With Nucleic Acid Probes, Part I. Theory and Nucleic Acid Preparation, Tijssen, ed. Elsevier, N.Y. (1993), all of which are herein incorporated by reference in their entirety).

In aspects, the present disclosure is directed to expression cassettes comprising a promoter operably linked to a heterologous nucleotide sequence of the instant disclosure that encodes an antipathogenic polypeptide are further provided. The expression cassettes may find use in generating transformed plants, plant cells, and microorganisms and in practicing the methods for treating and inducing pathogen resistance disclosed herein. In aspects, the expression cassette may include 5' and 3' regulatory sequences operably linked to a polynucleotide of the instant disclosure. "Operably linked" is intended to mean a functional linkage between two or more elements. For example, an operable linkage between a polynucleotide of interest and a regulatory sequence (i.e., a promoter) is functional link that allows for expression of the polynucleotide of interest. In aspects, operably linked elements may be contiguous or non-contiguous. When used to refer to the joining of two protein coding regions, by operably linked is intended that the coding regions are in the same reading frame. In aspects, the cassette may additionally contain at least one additional gene to be co-transformed into the organism. In aspects, alternatively, the additional gene(s) can be provided on multiple expression cassettes. In aspects, such an expression cassette may be provided with a plurality of restriction sites and/or recombination sites for insertion of the polynucleotide that encodes an antipathogenic polypeptide to be under the transcriptional regulation of the regulatory regions. In aspects, an expression cassette may additionally contain selectable marker genes.

In aspects, an expression cassette may include in the 5'-3' direction of transcription, a transcriptional initiation region (i.e., a promoter), translational initiation region, a polynucleotide of the invention, a translational termination region and, optionally, a transcriptional termination region functional in the host organism. In aspects, the regulatory regions (i.e., promoters, transcriptional regulatory regions, and translational termination regions) and/or the polynucleotide of the instant disclosure may be native/analogous to the host cell or to each other. In aspects, alternatively, the regulatory regions and/or the polynucleotide of the instant disclosure may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

Compositions and Formulations

In aspects, the present disclosure is directed to antipathogenic compositions or formulations comprising: one or more polypeptides, microorganisms that express one or more polypeptides, and/or nucleic acids of the present disclosure as previously described; and a carrier and/or excipient. These compositions possess the desired biological activity of the included polypeptides and/or nucleotides of the instant-disclosure, that is, antipathogenic activity, antifungal activity, antialgal activity, and/or enzymatic activity against chitin and/or polyglucuronic acid as described herein. As such, these compositions can be used in treating products, including agricultural products, from pathogens, including fungi and algae, as well as generating pathogen-resistant products (particularly fungi and algae-resistant products). In aspects, a polypeptide of the present disclosure is present in the antipathogenic composition at a concentration range of from about 0.1 microgram per milliliter to about 100 milligrams per milliliter, including any value or range therebetween. Acceptable carriers and/or excipients are determined in part by the particular composition being administered, as well as by the particular method used to administer the composition. For example, an acceptable carrier can include a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

In aspects, the antipathogenic compositions or formulations of the instant disclosure may comprise one or more solvents. The amount of solvents in the composition may range from 1% to 99%, or from 30% to 80%, or any value or range therebetween. Suitable solvents include, for example, a water-based salt solution (e.g., phosphate-buffered saline) a non-polar water-immiscible solvent, or a polar aprotic water miscible organic solvent. Non-polar solvents include, for example substituted or unsubstituted aliphatic or aromatic hydrocarbons and esters of plant oils or mixtures thereof. Non-limiting examples of aromatic hydrocarbons include benzene or substituted benzene derivatives such as toluene, xylene, 1,2,4-trimethylbenzene, naphthalene or mixtures thereof. In one embodiment, a solvent includes a mixture of napthalen and 1,2,4-trimethylbenzene. In another embodiment, a solvent is Aromatic 150, a heavy aromatic naptha solvent containing <10% naphthalene and <1.7% 1,2,4-trimethylbenzene. Alkyl esters can also be used as non-polar, water immiscible solvents. Plant oils may be esterified with various alcohols to form alkyl esters of plant oils. Fatty acids of these plant oils have 5 to 20, or 6 to 15 carbon atoms. Alkyl esters of plant oils include, without limitation, methyl, ethyl and butyl esters of canola (*B. napus*), linseed, safflower (Carthamus tinctorius L), soybean and sunflower oils. In one embodiment, the solvent is a mixture of methyl esters. A specific non-limiting example of methyl esters is Agent 2416-21 manufactured by Stepan Company (22 W. Frontage Road, Northfield, Ill.). Water-miscible polar aprotic solvents can include, for example, alkyl lactates, isopropyl lactate, alkyl carbonates, polyethylene glycols, polyethylene glycol alkyl ethers, polypropylene glycols, and polypropylene glycol alkyl ethers, or mixtures thereof. In aspects, the pH of the antipathogenic composition of the present disclosure is in the range of from about 4.0 to about 9.0, including any value or range therebetween.

In aspects, the composition of the present disclosure further comprises at least one additional compound, including a sticking agent, a carrier, a coloring agent, a protective colloid, an adhesive, a herbicide, a fertilizer, a thickening agent, a sequestering agent, a thixotropic agent, a surfactant, a detergent, a preservative, a spreading agent, a filler, a spray oil, a flow additive, a mineral substance, a solvent, a dispersant, an emulsifier, a wetting agent, a stabilizer, an antifoaming agent, a buffering agent, an UV-absorber and/or an antioxidant. In aspects, the additional compounds are additives acceptable for the specific use, e.g. food, feed, medicine, cosmetics, or agriculture. Additional compounds suitable for use in food, feed, medicine, cosmetics or agriculture are known to the person skilled in the art.

In aspects, the antipathogenic compositions or formulations of the instant disclosure may comprise one or more adjuvants. An adjuvant may enhance or improve antipathogenic activity, antifungal activity, antialgal activity, and/or enzymatic activity against chitin and/or polyglucuronic acid of the one or more polypeptides and/or nucleic acids of the present disclosure as described herein, for example. Adjuvants may be added to the composition at the time of formulation, or by the applicator to a mix prior to treatment. Adjuvants include, for example surfactants (emulsifier), crop oil, fertilizers, dispersing agents, compatibility agents, foaming activators, foam suppressants, correctives, and spray colorants (dyes). An adjuvant may be present in any desired amount. For example, a composition or formulation may contain 1% to 3% adjuvant, 3% to 8% of adjuvant, 8% to 16% adjuvant, 17% to 30% adjuvant, or 30% or (e.g. 40% or more) more adjuvant, including any value or range therebetween.

In aspects, the antipathogenic compositions or formulations of the instant disclosure may comprise one or more surfactants. A surfactant may increase solubility of the instantly-disclosed polypeptides in a solution. A surfactant may also affect spray retention, droplet spreading, and dry rates. A surfactant may be anionic or non-ionic. Examples of anionic surfactants include phosphoric mono- and di-esters of long-chain alcohols having 14 to 22 carbon atoms and the salts thereof; phosphoric mono- and di-esters of alkylene oxide addition products of long-chain alcohols having 14 to 22 carbon atoms and the salts thereof; alkylsulphates having 14 to 22 carbon atoms; polyoxyethylene alkyl ether sulphates of alcohols having 14 to 22 carbon atoms; alkane sulphonates having 14 to 22 carbon atoms; and olefin sulphonates having 14 to 22 carbon atoms. Suitable nonionic surfactants include, for example, ethoxylated fatty acids, alcohol ethoxylates, tristyrylphenol ethoxylates, ethoxylated sorbitan fatty acid esters or mixtures thereof. Ethoxylated fatty acids include castor or canola oil ethoxylates having at least 25, preferably 27 to 37 ethoxy units, such as Sunaptol® CA350 (castor oil ethoxylate with 35 ethoxy units) of Uniqema (formerly ICI Surfactants), Mergital® EL33 (castor oil ethoxylate with 33 ethoxy units) of Henkel KGaA, Eumulgin® Co3373 (canola oil ethoxylate with 30 ethoxy units) of Henkel KGaA and Ukanil® 2507 (castor oil ethoxylate) of Uniqema. Surfactants may be present in any desired amount. For example, a surfactant may be present in an amount of about 0.1 to about 30% by weight in the formulation, including any value or range therebetween.

In aspects, the antipathogenic compositions or formulations of the instant disclosure may comprise one or more emulsifiers. An emulsifier is a type of surfactant typically used to keep an emulsion well-dispersed. Non-limiting examples of the emulsifier include Agent 2201-76, Agent 2416-20, Emulpon CO-360, T-Det C-40®, and Agnique™ SBO-IO. Agent 2201-76 is manufactured by Stepan Company (22 W. Frontage Road, Northfield, Ill.), which is a blend of nonionic and anionic surfactants (82%). The ingredients in Agent 2201-76 are alkylbenzene sulfonate and fatty acid ethoxylate, aromatic petroleum hydrocarbon, 1-hexanol and naphthalene. Agent 2416-20 is also manufactured by Stepan Company (22 W. Frontage Road, Northfield, Ill.), which is a blend of nonionic and anionic surfactants (35-37%). Agent 2416-20 also includes aromatic petroleum hydrocarbon (57-58%), and naphthalene (6-7%). Emulpon CO-360 is manufactured by Akzo Nobel Chemicals Ltd. (525 West Van Buren, Chicago, Ill.), which contains ethoxylated castor oil (100% by weight) and oxirane (<0.001% by weight). T-Det C-40® may be purchased from Harcros Organics (5200 Speaker Road., P.O. Box 2930, Kansas City, Kans.), or from Akzo Nobel Chemicals Ltd. (525 West Van Buren, Chicago, Ill.), which is a non-ionic emulsifier, and a brand of ethoxylated (polyethoxylated) castor oil. Agnique™ SBO-IO is manufactured by Cognix GmbH headquartered in Monheim, Germany, which contains alkoxylated triglycerides as an ethoxylated soybean oil.

In aspects, the antipathogenic compositions or formulations of the instant disclosure may comprise a crop oil, or a crop oil concentrate, which may be used to increase the efficacy of a herbicide formulation. Although not wishing to be bound by any particular theory, a crop oil is believed to keep the an agricultural product, such as a leaf surface, moist longer than water, which in turn allows more time for the polypeptide or nucleotide to penetrate, thereby increasing the amount of polypeptide or nucleotide of the composition that will enter the agricultural product (e.g., plant). A crop oil can improve uptake of the polypeptide or nucleotide of the composition by the agricultural product (e.g., plant). A crop oil can therefore improve, enhance, increase or promote antipathogenic activity, antifungal activity, antialgal activity, and/or enzymatic activity against chitin and/or polyglucuronic acid as described herein. Crop oils may contained from 1% to 40% by weight, or 1% to 20% by weight in the composition, including any value or range therebetween. A crop oil can be derived from either petroleum oil or vegetable oil. Non-limiting examples of crop oil include soybean oils and petroleum based oils.

In aspects, the antipathogenic compositions or formulations of the instant disclosure may include colorants. Non-limiting examples are inorganic pigments, such as iron oxide, titanium oxide and Prussian Blue, and organic dyestuffs, such as alizarin dyestuffs, azo dye-stuffs and metal phthalocyanine dyestuffs, and trace nutrients such as salts of iron, manganese, boron, copper, cobalt, molybdenum and zinc.

In aspects, the antipathogenic composition my further comprise one or more additional active agents, such as pesticides, fertilizers, insecticides, attractants, sterilizing agents, acaridices, nematocides, herbicides, other fungicides, bactericides, harvest aids, and/or growth regulators. Such additional active agents can be combined with carriers, surfactants, or agents as is known in the art. The compositions of the instant disclosure may be applied simultaneously or in succession with such additional active agents.

In aspects, the antipathogenic compositions or formulations of the instant disclosure may be in customary formulations. The compositions may be solid or may be a liquid. Non-limiting examples include solutions, emulsions, suspensions, wettable powders, powders, dusts, pastes, soluble powders, granules, pellets, emulsifiable concentrate, oil spray, aerosol, natural and synthetic materials impregnated with active compound, and very fine capsules (e.g. in polymeric substances). In aspects, the antipathogenic compositions or formulations of the instant disclosure may optionally include adherent coatings. Such coatings include those that aid the polypeptides or nucleotides of the composition to adhere to the intended environment, for example, an agricultural product being treated. Adherent coatings include carboxymethylcellulose, natural and synthetic polymers in various forms, such as powders, granules or latexes. Other adherent coatings include gum arabic, polyvinyl alcohol and polyvinyl acetate. Phospholipids, such as cephalins and lecithins, and synthetic phospholipids are also examples of adherent coatings.

In aspects, the antipathogenic composition according to the instant disclosure can be applied in the form of ready mixes, such as aqueous or non-aqueous ready-to-use compositions. In aspects, the compositions can be used as such, in the form of their formulations or in the forms prepared therefrom by dilution of a concentrated form (such as aqueous or non-aqueous concentrated compositions/suspensions or stock compositions, suspensions and/or solutions which before use have to be diluted with a suitable diluent such as water or a buffer system), such as ready-to-use or concentrated liquids, solutions, suspensions, emulsions, or solids, such as, powders, pastes, granules and pellets. The compositions may be dispersed in the customary manner, for example by watering, spraying, atomizing, dusting or scattering.

In a further aspect, the instant disclosure relates to a kit comprising one or more polypeptides, microorganism that expresses one or more polypeptides, nucleic acids (and carriers of such nucleic acid as previously described, such as expression cassettes, expression vectors, recombinant viruses, etc.), and/or antipathogenic compositions of the present disclosure as previously described. The components of the kit may be either in dry form or liquid form in the package. If necessary, the kit may comprise instructions for dissolving the compounds. In addition, the kit may contain instructions for applying the compounds Method of Use The compounds and compositions of the instant disclosure as previously described find use in protecting/treating products, including but not limited to an agricultural product and a water body (e.g., including drinking water, such as tap water), from pathogens, including fungi and algae, as well as generating pathogen-resistant products (particularly fungi and algae-resistant products).

In aspects, the present disclosure is directed to methods for treating or protecting a product against a pathogen, such as fungi or algae (including harmful algal blooms), the method comprising applying or contacting one or more polypeptides, microorganism that expresses one or more polypeptides, polynucleotides, expression cassettes, plasmids, expression vectors, recombinant viruses and/or antipathogenic compositions of the present disclosure (hereafter referred to as "compounds or compositions") of the present disclosure as previously described to the product. "Treating or protecting a product against a pathogen", or the like, is intended to mean killing the pathogen or preventing, ameliorating, or limiting disease formation on or in a product. In addition, the product can be treated with other active agents, such as but not limited to other antifungal, antialgal, and/or antimicrobial compounds either prior to, concomitant with or after treatment of the products with the one or more compounds or compositions of the present disclosure as previously described. In aspects, the present disclosure is directed to a process for the protection or treatment of products by applying one or more compounds or compositions of the present disclosure to the products. By applying these compounds or compositions, fungal and/or algal growth on or in the products can be prevented. In other words, these compositions or compounds protect the products from fungal and or algal growth, fungal and/or algal infection, and/or from fungal and/or algal spoilage. Thus, in aspect, the compounds and compositions of the present disclosure find use in methods for inducing pathogen resistance in a product. Accordingly, the compounds, compositions and methods disclosed herein are useful in protecting products again pathogens, particularly fungi and algae. "Pathogen resistance" or "disease resistance" is intended to mean that the product avoids the disease symptoms that are the outcome of pathogen interactions. That is, the pathogens are prevented from causing diseases and the associated disease symptoms, or alternatively, the disease symptoms caused by the pathogen are minimized or lessened, such as, for example, the reduction of stress and associated yield loss. Therefore, in aspects, the present disclosure is directed to methods for inducing pathogen resistance in a product, the method comprising applying or contacting one or more compounds or compositions of the present disclosure to the product. One of skill in the art will appreciate that the compounds or compositions and methods disclosed herein can be used with other compositions and methods available in the art for protecting plants from insect and pathogen attack. The compounds or compositions of the instant disclosure can also be used to treat products that have been infected with a fungus and or alga. By applying these compounds or compositions, the disease development due to fungi and/or algae on or in these products can be slowed down, stopped, or the products may even be cured from the disease. In aspects, the products are treated with these compounds or compositions according to the instant disclosure, e.g., by applying or contacting the compounds or compositions to the product. In aspects, the product is a water body (e.g., including drinking water, such as tap water), food, feed, or agricultural product.

Compounds or compositions of the instant disclosure find use in protecting products in a variety of ways. For example, the compounds or compositions can be used in a method that involves placing an effective amount of the antipathogenic, more particularly, antifungal and/or antialgal, composition to the product to be treated and/or to the environment of the pathogen, including by spraying, dusting, broadcasting, foliage application, soil application, or seed coating. As used herein, an "effective amount" is intended to mean an amount of the compounds or compositions sufficient to control the pathogen. Other methods suitable for applying these compounds or compositions to a product or the environment of a pathogen, particularly in liquid form, are also a part of the present disclosure. These include, but are not limited to, dipping, watering, drenching, introduction into a dump tank, vaporizing, atomizing, fogging, fumigating, painting, brushing, dusting, foaming, spreading-on, packaging and coating (e.g. by means of wax or electrostatically). In addition, these compounds or compositions may also be injected into the soil or a water body. To be clear, compounds and compositions of the instant disclosure can be used for any application including coating surfaces to target pathogens, particularly fungi and algae. Polymer bound polypeptides of the invention may be used to coat surfaces. Methods for incorporating compounds or compositions of the present disclosure are known in the art.

In aspects, the methods of the instant disclosure are directed to introducing a polypeptide or polynucleotide of the invention into a product, particularly water body (e.g., including drinking water, such as tap water), food, feed, or agricultural product. As used herein, "introducing" is intended to mean presenting to the product the polynucleotide. In aspects, the polynucleotide will be presented in such a manner that the sequence gains access to the interior of product, such as a cell of the agricultural product (e.g., plant), including its potential insertion into the genome of an agricultural product (e.g., plant). In aspects, the methods of the instant disclosure do not depend on a particular method for introducing a sequence into a product, such as a cell of the agricultural product (e.g., plant), only that the polynucleotide gains access to the interior of at least one cell of the agricultural product (e.g., plant). Methods for introducing polynucleotides into agricultural products (e.g., plant) are known in the art including, but not limited to, stable transformation methods, transient transformation methods, and virus-mediated methods. Polypeptides can also be introduced to agricultural products (e.g., plant) in such a manner that they gain access to the interior of the agricultural product cell (e.g., plant cell) or remain external to the cell but in close contact with it.

As used herein, "stable transformation" is intended to mean that the nucleotide construct introduced into an agricultural product (e.g., plant) integrates into the genome of the agricultural product (e.g., plant) and is capable of being inherited by the progeny thereof "Transient transformation" or "transient expression" is intended to mean that a polynucleotide is introduced into the agricultural product (e.g., plant) and does not integrate into the genome of the agricultural product (e.g., plant) or a polypeptide is introduced into an agricultural product (e.g., plant).

In specific embodiments, the antipathogenic sequences of the invention can be provided to an agricultural product (e.g., plant) using a variety of transient transformation methods. Such transient transformation methods include, but are not limited to, the introduction of the antipathogenic protein or variants and fragments thereof directly into the agricultural product (e.g., plant) or the introduction of the antipathogenic protein transcript into the agricultural product (e.g., plant) using techniques known in the art. Alternatively, the polynucleotide can be transiently transformed into the agricultural product (e.g., plant) using techniques known in the art. Such techniques include viral vector system and the precipitation of the polynucleotide in a manner that precludes subsequent release of the DNA. Thus, the transcription from the particle-bound DNA can occur, but the frequency with which it's released to become integrated into the genome is greatly reduced.

In other aspects, a polynucleotide of the instant disclosure may be introduced into an agricultural product (e.g., plant) by contacting the agricultural product (e.g., plant) with a virus or viral nucleic acids. In aspects, such methods involve incorporating a nucleotide construct of the invention within a viral DNA or RNA molecule. Methods for introducing polynucleotides into an agricultural product (e.g., plant) and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) Molecular Biotechnology 5:209-221; herein incorporated by reference.

In aspects, the presently disclosed compounds and compositions and methods display antifungal activity to a wide range of pathogenic fungi. In aspects, the compounds and compositions and methods display antifungal activity against the following fungi: Blumeria spp., e.g. Blumeria graminis; Uncinula spp., e.g. Uncinula necator; Leveillula spp., e.g. Leveillula taurica; Podosphaera spp., e.g. Podosphaera leucotricha, Podosphaera fusca, Podosphaera aphanis; Microsphaera spp., e.g. Microsphaera syringae; Sawadaea spp., e.g. Sawadaea tulasnei; Mycosphaerella spp., Mycosphaerella musae, Mycosphaerella fragariae, Mycosphaerella citri; Mucor spp., e.g. Mucor piriformis; Monilinia spp., e.g. Monilinia fructigena, Monilinia laxa; Phomopsis spp., Phomopsis natalensis; Colletotrichum spp., e.g. *Colletotrichum musae, Colletotrichum gloeosporioides, Colletotrichum coccodes; Verticillium* spp., e.g. *Verticillium theobromae; Nigrospora* spp.; *Botrytis* spp., e.g. *Botrytis cinerea; Diplodia* spp., e.g. *Diplodia citri; Pezicula* spp.; *Alternaria* spp., e.g. *Alternaria citri, Alternaria alternata; Septoria* spp., e.g. *Septoria depressa; Venturia* spp., e.g. *Venturia inaequalis, Venturia pyrina; Rhizopus* spp., e.g. *Rhizopus stolonifer, Rhizopus oryzae; Glomerella* spp., e.g. *Glomerella cingulata; Sclerotinia* spp., e.g. *Sclerotinia fruiticola; Ceratocystis* spp., e.g. *Ceratocystis paradoxa; Fusarium* spp., e.g. *Fusarium semitectum, Fusarium moniliforme, Fusarium solani, Fusarium oxysporum; Cladosporium* spp., e.g. *Cladosporium fulvum, Cladosporium cladosporioides, Cladosporium cucumerinum, Cladosporium musae; Penicillium* spp., e.g. *Penicillium funiculosum, Penicillium expansum, Penicillium digitatum, Penicillium italicum; Phytophthora* spp., e.g. *Phytophthora citrophthora, Phytophthora fragariae, Phytophthora cactorum, Phytophthora parasitica*; Phacydiopycnis spp., e.g. Phacydiopycnis malirum; *Gloeosporium* spp., e.g. *Gloeosporium album, Gloeosporium perennans, Gloeosporium fructigenum, Gloeosporium singulata; Geotrichum* spp., e.g. *Geotrichum candidum*; Phlyctaena spp., e.g. Phlyctaena *vagabunda; Cylindrocarpon* spp., e.g. *Cylindrocarpon mali*; Stemphyllium spp., e.g. Stemphyllium *vesicarium; Thielaviopsis* spp., e.g. *Thielaviopsis* paradoxy; *Aspergillus* spp., e.g. *Aspergillus niger, Aspergillus carbonarius; Nectria* spp., e.g. *Nectria galligena; Cercospora* spp., e.g. *Cercospora angreci, Cercospora apii, Cercospora atrofiliformis, Cercospora musae, Cercospora zeae-maydis; Botrytis* spp.; *Mucor* spp.; *Talaromyces* spp.; *Verticillium* spp.; Chaetomeum spp.; *Issatchenkia* spp.; Gelainspora spp.; *Macrophomina* spp.; Anthracnose spp.; *Sphaerotheca* spp.; *Guignardia* spp.; *Fusicoccum* spp.; Paecilomyes spp.; and *Byssochlamys* spp. In particular aspects, the compounds and compositions and methods display antifungal activity against the following fungi: *Botrytis* spp.; *Mucor, Cladosporium* spp.; *Fusarium* spp.; *Talaromyces* spp.; *Rhizopus* spp.; *Verticillium* spp.; Chaetomeum *Issatchenkia* spp.; Gelainspora spp.; *Macrophomina* spp.; Anthracnose spp.; *Podosphaera* spp.; *Sphaerotheca* spp.; *Penicillium* spp.; *Aspergillus* spp.; *Uncinula* spp.; *Guignardia* spp.; *Fusicoccum* spp.; Paecilomyes spp.; *Byssochlamys* spp.; and Mucoraceae spp.

In aspects, the presently disclosed compounds and compositions and methods display antialgal activity to a wide range of algae, including harmful algae and harmful algal blooms, including but not limited to: *Alexandrium* spp.; *Gymnodinium* spp.; *Karenia* mikimotoi, *Pseudonitzschia* spp.; *Karenia* seleniformes, *Karenia* bidigigata, Pyrodininum spp.; Gonyaulax spp.; *Ceratium* spp.; Lingulodinium, Chattonella spp.; Akashiwo spp.; *Gyrodinium* spp.; Pfisteria spp.; Prorocentrum spp.; Dinophysis, *Heterocapsa*, Scripssiella, *Karenia brevis*, Protoperidinium spp.; and *Microcystis aeruginosa.*

The term "food products" as used herein is to be understood in a very broad sense and includes, but is not limited to, cheese, cream cheese, shredded cheese, cottage cheese processed cheese, sour cream, dried fermented meat product including salamis and other sausages, wine, beer, yoghurt, juice and other beverages, salad dressing, cottage cheese dressing, dips, bakery products and bakery fillings, surface glazes and icing, spreads, pizza toppings, confectionery and confectionery fillings, olives, olive brine, olive oil, juices, tomato purees and paste, condiments, and fruit pulp and the like food products.

The term "feed products" as used herein is also to be understood in a very broad sense and includes, but is not limited to, pet food, broiler feed, etc.

The term "agricultural products" as used herein is also to be understood in a very broad sense and includes, but is not limited to, cereals, e.g. wheat, barley, rye, oats, rice, sorghum and the like; grains; beets, e.g. sugar beet and fodder beet; pome and stone fruit and berries, e.g. apples, pears, plums, apricots, peaches, almonds, cherries, strawberries, raspberries and blackberries; leguminous plants, e.g. beans, lentils, peas, soy beans; oleaginous plants, e.g. rape, mustard, poppy, olive, sunflower, coconut, castor-oil plant, cocoa, ground-nuts; cucurbitaceae, e.g. pumpkins, gherkins, melons, cucumbers, squashes, aubergines; fibrous plants, e.g. cotton, flax, hemp, jute; citrus fruit, e.g. oranges, lemons, grapefruits, mandarins, limes; tropical fruit, e.g. papayas, passion fruit, mangos, carambolas, pineapples, bananas, kiwis; vegetables, e.g. spinach, lettuce, asparagus, brassicaceae such as cabbages and turnips, carrots, onions, tomatoes, potatoes, seed-potatoes, hot and sweet peppers; laurel-like plants, e.g. avocado, cinnamon, camphor tree; or products such as maize, tobacco, nuts, coffee, sugarcane, tea, grapevines, hops, rubber plants, as well as ornamental plants, e.g. cut flowers, roses, tulips, lilies, narcissus, crocuses, hyacinths, dahlias, gerbera, carnations, fuchsias, chrysanthemums, and flower bulbs, shrubs, deciduous trees and evergreen trees such as conifers, plants and trees in greenhouses. It includes, but is not limited to, plants and their parts, fruits, seeds, cuttings, cultivars, grafts, bulbs, tubers, root-tubers, rootstocks, cut flowers and vegetables. The term plant includes plant cells, plant protoplasts, plant cell tissue cultures from which maize plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the instant, provided that these parts comprise the introduced polynucleotides.

EXAMPLES

The following examples are given by way of illustration and are in no way intended to limit the scope of the present invention.

Example 1

Materials and Methods

Unless specified otherwise, the following experimental techniques were used in the Examples.

Mutagenesis Design:

Rational design of the active site was guided by prior research by the Berger group to characterize catalytic and substrate binding residues within the active site of the wild type (WT) Smlt2602; UniProt ID B2FSW8 (L. C. Macdonald, B. W. Berger, Insight into the role of substrate-binding residues in conferring substrate specificity for the multifunctional polysaccharide lyase Smlt1473, J. Biol. Chem. 289 (2014) 18022-18032, herein incorporated by reference in its entirety). Previously pursued mutations aimed to identify the importance of core active site residues in substrate binding and catalytic activity on a number of substrates including alginate, mannuronic acid, guluronic acid, and polyglucuronic acid. A similar strategy was employed to explore residues involved in binding and positioning of the newly discovered active substrate, chitin. Beyond screening the prior disclosed mutations, additional residues within the active site were identified as targets to improve substrate activity through homology modeling. In total, 44 residues were selected based on their 1) proximity to the active site, 2) side group chemistry, and 3) orientation within the active site.

In general, aromatic residues (Histidine, Tryptophan, Tyrosine) were selected for their known role in positioning of substrate in carbohydrate processing enzymes, and modified to alternate aromatic groups. Additional residues, including positively charged and polar residues, were selected for both conservative and non-conservative mutations to introduce promiscuity among variants with the aim of shifting specific activity towards the substrate of interest, chitin.

Protein Expression, Purification, and Analysis Protocol:

Expression plasmids and methods for enzyme overexpression have been described in detail previously (L. C. Macdonald, B. W. Berger, Insight into the role of substrate-binding residues in conferring substrate specificity for the multifunctional polysaccharide lyase Smlt1473, J. Biol. Chem. 289 (2014) 18022-18032, herein incorporated by reference in its entirety). In summary, Smlt2602 WT (UniProt ID B2FSW8) was subcloned into pET28a vectors as BamHI-XhoI inserts, which includes a C-terminal hexahistidine tag for purification, and transformed into BL21 (DE3) pLysS cells by electroporation.

Mutagenic primers were designed via PrimerX, and amino acid substitutions were generated via the QuikChange II site-directed mutagenesis kit (Agilent Technologies). Nucleotide sequences containing mutations were confirmed by DNA sequencing (GeneWiz). Following sequence confirmation, mutated plasmids were then transformed into BL21 cells by electroporation.

Individual colonies were isolated from kanamycin-selective plates (50 g/mL working concentration), inoculated in 20 mL LB cultures containing kanamycin, and grown to saturation at 37 C with 200 rpm agitation in a shaking incubator (Innova R26). Cell mass from saturated cultures were collected by centrifugation at 3000 g for 10 min, spent media decanted, and resuspended in 100 mL of fresh LB media containing kanamycin in 500 mL flasks to an OD600 of 0.4. Cultures were grown at 37 C, 250 rpm agitation and OD600 was used to monitor cell growth. At an OD600 of 0.6, IPTG was added to a final concentration of 1 mM to induce protein expression and cultures were transferred to 20 C, 250 rpm agitation. Cells were harvested after 24 h growth at 20° C. with 250 rpm agitation by centrifugation at 3000 rpm for 10 min.

Cell pellets from 50 mL of induced culture were resuspended in 20 mL of lysis buffer (100 mM NaCl, 50 mM Tris pH=8, 5 mM imidazole). Homogenization (Avestin Emulsiflux) was used to lyse the cells within the 20 mL of buffer. The lysis mixture was centrifuged at 12000 g for 10 min, insoluble material was discarded and the soluble supernatant containing enzyme collected. The enzyme was purified using immobilized metal ion affinity chromatography (IMAC) with 2 mL of Profinity resin. The column was charged with a 0.2 M nickel chloride solution and equilibrated with two column volumes of lysis buffer prior to running the cell lysate. The column was initially washed with two column volumes of 10 mM imidazole and collected. Then, imidazole concentrations of 250 mM and 500 mM were used to elute the protein and 5 mL fractions collected. SDS-PAGE was used to confirm purification and purity of final enzyme product. Protein samples (40 L) were mixed with 10 L of 5× Lammeli sample buffer and heated for 5 min at 95° C. before loading onto a 4% stacking, 12% separating acrylamide gel with IVIES running buffer. Precision Plus Protein All Blue Standard (Bio-Rad) was used as a molecular weight standard. The gel was run at 100 V for 15 min and then at 175 V for 40 min. The gel was then stained with Coomassie Blue stain (1 g Coomassie Brilliant Blue (Bio-Rad), 1:4:5 acetic acid, methanol, double-distilled H2O; ddH2O) for 2 h and then destained with a solution of 1:2:7 acetic acid, methanol and ddH2O. Eluates containing purified protein were dialyzed for 24 h at 4° C. with a 3500 MWC ThermoFisher Snakeskin dialysis membrane in 4 L of 20 mM pH 8.25 phosphate buffer to yield a purified product. Enzyme concentration was then measured in triplicate using absorbance at 280 nm with an extinction coefficient of 103710 M-1 cm-1.

Schales' Assay for Antifungal Activity Screening:

To demonstrate changes to substrate activity correlating with antifungal activity, mutant enzymes were combined with chitin in a 200 µL reaction mixture containing 3 mg/mL colloidal chitin, 20 mM phosphate buffer pH 8, and 0.05 mg/mL enzyme. The control group contained all reaction components and dialysis buffer solution to replace enzyme solution. The reaction was incubated at 30° C. and 300 rpm for 1 hr. The suspension was then centrifuged to remove insoluble chitin and 100 µL of supernatant was added to 100 µL Schales' reagent (0.5 M sodium carbonate and 0.5 g/L potassium ferricyanide). The sample was incubated at 100° C. for 15 min and cooled to 20° C. Absorbance at 420 nm was measured for each sample. Decrease in absorbance from the control indicated chitinase activity and was expressed as a change from the control, as well as a change from the WT to determine increased or decreased variant activity. Reactions were performed in triplicate and standard error was reported.

Antifungal Plate Assay:

Fungal spores were transferred to a potato dextrose agar (PDA) plate (3 samples in each group). In the control group, spores were then spotted with 5 µL of control buffer while the enzyme treated samples were spotted with 5 µL of enzyme solution at a concentration of 1 mg/mL. Growth was monitored for 3 days. Effectiveness of treatment was rated on a scale from 0 to 3 with 3 being the highest efficacy.

Beta Elimination Assay for Algaecidal Activity Screening:

The A235 assay measures the accumulation of the unsaturated double bond produced by the enzyme's beta-elimination mechanism on polyglucuronic acid (PolyGlcA). To demonstrate changes to substrate activity correlating with algaecidal activity, mutant enzymes were combined with polyGlcA in a 200 µL reaction mixture containing 3 mg/mL polyGlcA, 20 mM phosphate buffer pH=8, and 0.05 mg/mL enzyme. The control group contained all reaction components and dialysis buffer solution to replace enzyme solution. Reactions were mixed and then immediately transferred to a UV-clear 96 well plate. Change in absorbance at 235 nm was measured in 30 second intervals over 10 minutes. The slope of the linear portion of the curve correlates to enzyme activity, which was compared to that of the wild type. Reactions were performed in triplicate and standard error was reported.

Example 2

Results

Figure 2:
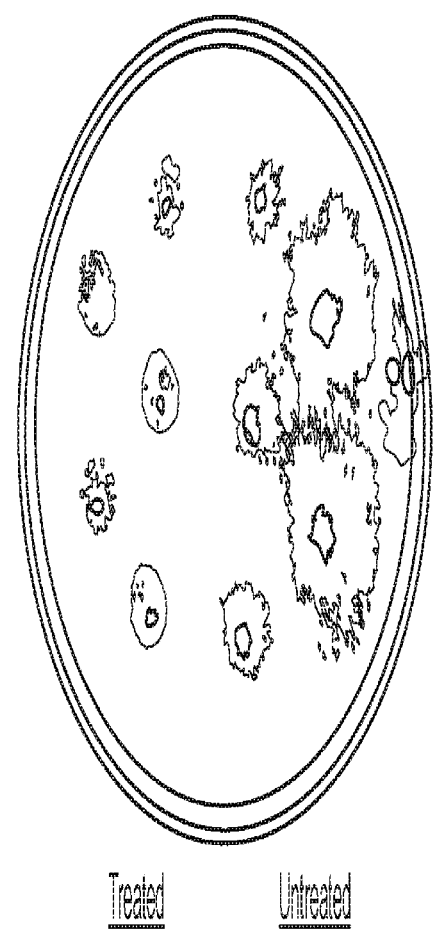
FIG. 2 shows an antifungal plate assay indicating efficacy of a genetically modified polysaccharide lyase polypeptides from *Stenotrophomonas maltophilia* (Smlt2602; UniProt ID B2FSW8).
Figure 3:
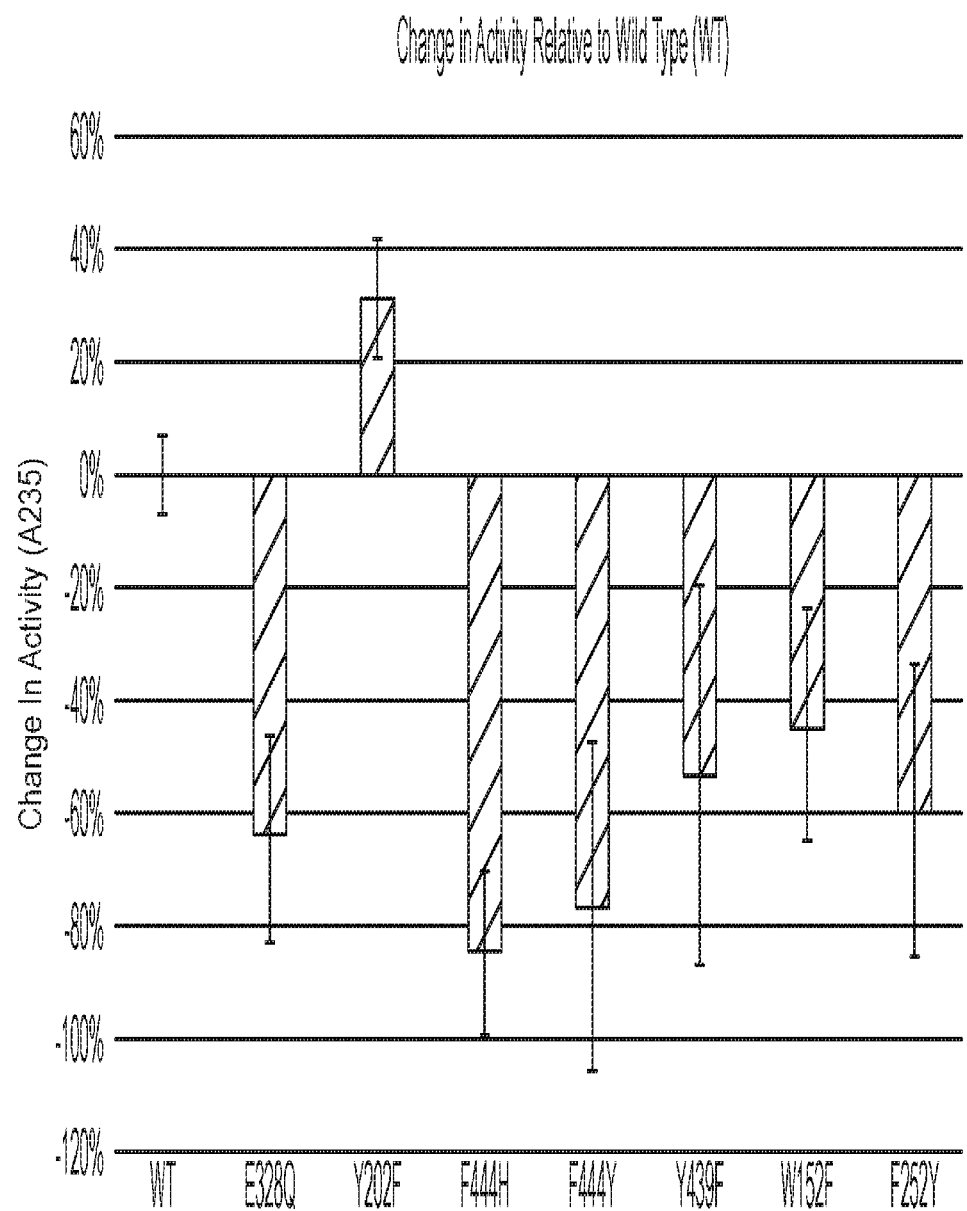
FIG. 3 shows a beta elimination assay for antialgal activity screening for the wild type and various genetically modified polysaccharide lyase polypeptides from *Stenotrophomonas maltophilia* (Smlt2602; UniProt ID B2FSW8).

Overall, previously disclosed mutants, including core binding and catalytic residues, displayed significant or complete loss of chitinase activity relative to the WT (FIG. 1). However, mutants Q153A and Y455F displayed slight but significant increases in activity (FIG. 1). Among novel modified residues, which were located within the active site but further from the core catalytic and binding residues, somewhat decreased or equivalent activity was observed relative to the WT in most cases. Novel targeted residues leading to the greatest change in activity include R443L, N446L, W152F and Y202F (FIG. 1). R443L and N446L led to significant decreases in activity while W152F and Y202F led to significant increases in activity (FIG. 1). It should be noted that residues W152F, R443L, N446L, Y455F, and Q153A outline the tunnel conformation of the active site in close proximity with 4 to 10 angstroms between adjacent residues. Significant change in chitin activity due to modification of these residues indicates importance of this region at the entrance of the active site in chitin binding and positioning. The significant increase in activity demonstrated by W152F supports initial assumptions in the important role of aromatic groups in conferring substrate specificity. Improved activity demonstrated by Y202F also supports the approach, although the residue lies at the opposite end of the active site relative to the other significant residues identified. Further, antifungal plate assays treated with W152F displayed significant reduction in growth and sporulation of *Botrytis* cineria when compared to the buffer-treated control (FIG. 2). Additionally, Y202F and the combination of Y202F and H208F showed significant increase in antialgal activity as shown in the beta-elimination assay (FIG. 3 and data not shown).

Various modifications of the present invention, in addition to those shown and described herein, will be apparent to those skilled in the art of the above description. Such modifications are also intended to fall within the scope of the appended claims.

It is appreciated that all reagents are obtainable from commercial sources known in the art unless otherwise specified.

Patents, publications, and applications mentioned in the specification are indicative of the levels of those skilled in the art to which the invention pertains. These patents, publications, and applications are incorporated herein by reference to the same extent as if each individual patent, publication, or application was specifically and individually incorporated herein by reference.

The foregoing description is illustrative of particular aspects of the invention, but is not meant to be a limitation upon the practice thereof

The invention claimed is:

1. A genetically modified polysaccharide lyase polypeptide comprising an amino acid sequence having at least 85% sequence identity to SEQ ID NO: 1 and comprising a mutation, wherein the mutation is selected from the group consisting of W152F, Y202F, Q153A, or a combination thereof, and wherein the polypeptide has antifungal activity.

2. The genetically modified polysaccharide lyase polypeptide of claim 1, further comprising the mutation H208F and/or Y455F.

3. The genetically modified polysaccharide lyase polypeptide of claim 1, wherein the mutation is W152F.

4. The genetically modified polysaccharide lyase polypeptide of claim 1, wherein the mutation is Y202F.

5. The genetically modified polysaccharide lyase polypeptide of claim 1, wherein the mutation is Q153A.

6. The genetically modified polysaccharide lyase polypeptide of claim 1, further comprising the mutation Y455F.

7. A composition comprising: the polypeptide of claim 1 and a carrier.

8. The composition of claim 7, wherein the amount of the polypeptide is present at a concentration range of from about 0.1 microgram per milliliter to about 100 milligrams per milliliter.

9. The composition of claim 7, wherein the pH of the composition is from about 4 to about 9.

10. The composition of claim 7, wherein the composition further comprises one or more additional active agents.

11. The composition of claim 10, wherein the one or more additional active agents is selected from the group consisting of pesticides, fertilizers, insecticides, attractants, sterilizing agents, acaridices, nematocides, herbicides, other fungicides, bactericides, harvest aids, and growth regulators.

12. A polynucleotide encoding the polypeptide of claim 1.

13. A cell or microorganism comprising the polypeptide of claim 1.

14. A method of protecting a product against fungi or algae comprising applying or contacting the product with the polypeptide of claim 1.

15. A method of protecting a product against fungi or algae comprising applying or contacting the product with the composition of claim 7.

16. A method of protecting a product against fungi or algae comprising applying or contacting the product with the cell or microorganism of claim 13.

17. A method for inducing fungal or algal resistance in a product, the method comprising applying or contacting the product with the polypeptide of claim 1.

* * * * *